United States Patent
Marci et al.

(10) Patent No.: US 9,936,250 B2
(45) Date of Patent: Apr. 3, 2018

(54) METHODS AND APPARATUS TO ADJUST CONTENT PRESENTED TO AN INDIVIDUAL

(71) Applicant: The Nielsen Company (US), LLC, New York, NY (US)

(72) Inventors: Carl Marci, Boston, MA (US); Brian Levine, Newton, MA (US); Brendan Murray, Boston, MA (US)

(73) Assignee: THE NIELSEN COMPANY (US), LLC, New York, NY (US)

( * ) Notice: Subject to any disclaimer, the term of this patent is extended or adjusted under 35 U.S.C. 154(b) by 120 days.

(21) Appl. No.: 15/155,543

(22) Filed: May 16, 2016

(65) Prior Publication Data

US 2016/0345060 A1 Nov. 24, 2016

Related U.S. Application Data

(60) Provisional application No. 62/163,874, filed on May 19, 2015, provisional application No. 62/272,423, filed on Dec. 29, 2015.

(51) Int. Cl.
H04N 21/442 (2011.01)
H04N 21/4415 (2011.01)
(Continued)

(52) U.S. Cl.
CPC ....... *H04N 21/44218* (2013.01); *A61B 3/112* (2013.01); *A61B 3/113* (2013.01);
(Continued)

(58) Field of Classification Search
None
See application file for complete search history.

(56) References Cited

U.S. PATENT DOCUMENTS 2,549,836 A 4/1951 McIntyre et al.
3,490,439 A 1/1970 Rolston
(Continued)

FOREIGN PATENT DOCUMENTS

EP 1087618 3/2001
EP 1609418 12/2005
(Continued)

OTHER PUBLICATIONS

Aaker et al., "Warmth in Advertising: Measurement, Impact, and Sequence Effects," Journal of Consumer Research, vol. 12, No. 4, pp. 365-381, (Mar. 1986), 18 pages.
(Continued)

*Primary Examiner* — Ricky Chin
(74) *Attorney, Agent, or Firm* — Hanley, Flight & Zimmerman, LLC

(57) ABSTRACT

Methods, apparatus, systems and articles of manufacture to adjust content presented to an individual are disclosed. An example method includes measuring, via sensors, responses of an individual to content during a first time, determining response classifications based on a comparison of the responses and respective thresholds, determining a first mental classification of the individual based on combining the response classifications, determining a baseline during the first time, measuring additional responses to the content during a second time, determining additional response classifications based on a comparison of the additional responses to respective additional thresholds, adjusting the baseline based on the additional responses in the second time, determining a second mental classification of the individual based on combining the additional response classifications, determining a mental state of a user based on a similarity of the first mental classification and the second mental classification, and modifying the content based on the mental state.

20 Claims, 8 Drawing Sheets

(51) Int. Cl.
*H04N 21/422* (2011.01)
*G06F 3/01* (2006.01)
*G06K 9/00* (2006.01)
*A61B 5/053* (2006.01)
*A61B 3/11* (2006.01)
*A61B 3/113* (2006.01)
*A61B 5/16* (2006.01)
*H04N 21/81* (2011.01)
*G06Q 30/02* (2012.01)
*H04N 21/458* (2011.01)
*H04N 21/4223* (2011.01)
*A61B 5/00* (2006.01)

(52) U.S. Cl.
CPC .......... *A61B 5/0064* (2013.01); *A61B 5/0533* (2013.01); *A61B 5/165* (2013.01); *A61B 5/7282* (2013.01); *G06F 3/01* (2013.01); *G06K 9/00221* (2013.01); *G06K 9/00362* (2013.01); *G06Q 30/0201* (2013.01); *H04N 21/4223* (2013.01); *H04N 21/42201* (2013.01); *H04N 21/4415* (2013.01); *H04N 21/44204* (2013.01); *H04N 21/44213* (2013.01); *H04N 21/458* (2013.01); *H04N 21/812* (2013.01); *A61B 5/7278* (2013.01); *A61B 2503/12* (2013.01)

(56) References Cited

U.S. PATENT DOCUMENTS

| | | |
|---|---|---|
| 3,572,322 A | 3/1971 | Wade |
| 3,735,753 A | 5/1973 | Pisarski |
| 3,880,144 A | 4/1975 | Coursin et al. |
| 3,901,215 A | 8/1975 | John |
| 3,998,213 A | 12/1976 | Price |
| 4,075,657 A | 2/1978 | Weinblatt |
| 4,145,122 A | 3/1979 | Rinard et al. |
| 4,149,716 A | 4/1979 | Scudder |
| 4,201,224 A | 5/1980 | John |
| 4,279,258 A | 7/1981 | John |
| 4,411,273 A | 10/1983 | John |
| 4,417,592 A | 11/1983 | John |
| 4,537,198 A | 8/1985 | Corbett |
| 4,557,270 A | 12/1985 | John |
| 4,610,259 A | 9/1986 | Cohen et al. |
| 4,613,951 A | 9/1986 | Chu |
| 4,626,904 A | 12/1986 | Lurie |
| 4,632,122 A | 12/1986 | Johansson et al. |
| 4,683,891 A | 8/1987 | Cornellier et al. |
| 4,683,892 A | 8/1987 | Johansson et al. |
| 4,686,999 A | 8/1987 | Snyder et al. |
| 4,695,879 A | 9/1987 | Weinblatt |
| 4,736,751 A | 4/1988 | Gevins et al. |
| 4,800,888 A | 1/1989 | Itil et al. |
| 4,802,484 A | 2/1989 | Friedman et al. |
| 4,846,190 A | 7/1989 | John |
| 4,870,579 A | 9/1989 | Hey |
| 4,885,687 A | 12/1989 | Carey |
| 4,894,777 A | 1/1990 | Negishi et al. |
| 4,913,160 A | 4/1990 | John |
| 4,955,388 A | 9/1990 | Silberstein |
| 4,967,038 A | 10/1990 | Gevins et al. |
| 4,973,149 A | 11/1990 | Hutchinson |
| 4,987,903 A | 1/1991 | Keppel et al. |
| 5,003,986 A | 4/1991 | Finitzo et al. |
| 5,010,891 A | 4/1991 | Chamoun |
| 5,038,782 A | 8/1991 | Gevins et al. |
| 5,052,401 A | 10/1991 | Sherwin |
| 5,083,571 A | 1/1992 | Prichep |
| RE34,015 E | 8/1992 | Duffy |
| 5,137,027 A | 8/1992 | Rosenfeld |
| 5,213,338 A | 5/1993 | Brotz |
| 5,226,177 A | 7/1993 | Nickerson |
| 5,243,517 A | 9/1993 | Schmidt et al. |
| 5,273,037 A | 12/1993 | Itil et al. |
| 5,291,888 A | 3/1994 | Tucker |
| 5,293,867 A | 3/1994 | Oommen |
| 5,295,491 A | 3/1994 | Gevins |
| 5,331,544 A | 7/1994 | Lu et al. |
| 5,339,826 A | 8/1994 | Schmidt et al. |
| 5,345,281 A | 9/1994 | Taboada et al. |
| 5,357,957 A | 10/1994 | Itil et al. |
| 5,363,858 A | 11/1994 | Farwell |
| 5,392,788 A | 2/1995 | Hudspeth |
| 5,406,956 A | 4/1995 | Farwell |
| 5,410,609 A | 4/1995 | Kado et al. |
| 5,436,830 A | 7/1995 | Zaltman |
| 5,447,166 A | 9/1995 | Gevins |
| 5,474,082 A | 12/1995 | Junker |
| 5,479,934 A | 1/1996 | Imran |
| 5,513,649 A | 5/1996 | Gevins et al. |
| 5,518,007 A | 5/1996 | Becker |
| 5,537,618 A | 7/1996 | Boulton et al. |
| 5,540,285 A | 7/1996 | Alhamad |
| 5,550,928 A | 8/1996 | Lu et al. |
| 5,617,855 A | 4/1997 | Waletzky et al. |
| 5,655,534 A | 8/1997 | Ilmoniemi |
| 5,676,138 A | 10/1997 | Zawilinski |
| 5,676,148 A | 10/1997 | Koo et al. |
| 5,687,322 A | 11/1997 | Deaton et al. |
| 5,720,619 A | 2/1998 | Fisslinger |
| 5,724,987 A | 3/1998 | Gevins et al. |
| 5,726,701 A | 3/1998 | Needham |
| 5,729,205 A | 3/1998 | Kwon |
| 5,736,986 A | 4/1998 | Sever, Jr. |
| 5,740,035 A | 4/1998 | Cohen et al. |
| 5,762,611 A | 6/1998 | Lewis et al. |
| 5,771,897 A | 6/1998 | Zufrin |
| 5,774,591 A | 6/1998 | Black et al. |
| 5,787,187 A | 7/1998 | Bouchard et al. |
| 5,800,351 A | 9/1998 | Mann |
| 5,802,208 A | 9/1998 | Podilchuk et al. |
| 5,802,220 A | 9/1998 | Black et al. |
| 5,812,642 A | 9/1998 | Leroy |
| 5,817,029 A | 10/1998 | Gevins et al. |
| 5,842,199 A | 11/1998 | Miller et al. |
| 5,848,399 A | 12/1998 | Burke |
| 5,892,566 A | 4/1999 | Bullwinkel |
| 5,945,863 A | 8/1999 | Coy |
| 5,961,332 A | 10/1999 | Joao |
| 5,974,262 A | 10/1999 | Fuller et al. |
| 5,983,129 A | 11/1999 | Cowan et al. |
| 5,995,868 A | 11/1999 | Dorfmeister et al. |
| 6,001,065 A | 12/1999 | DeVito |
| 6,016,475 A | 1/2000 | Miller et al. |
| 6,021,346 A | 2/2000 | Ryu et al. |
| 6,032,129 A | 2/2000 | Greef et al. |
| 6,052,619 A | 4/2000 | John |
| 6,088,040 A | 7/2000 | Oda et al. |
| 6,099,319 A | 8/2000 | Zaltman et al. |
| 6,120,440 A | 9/2000 | Goknar |
| 6,128,521 A | 10/2000 | Marro et al. |
| 6,154,669 A | 11/2000 | Hunter et al. |
| 6,155,927 A | 12/2000 | Levasseur et al. |
| 6,161,030 A | 12/2000 | Levendowski et al. |
| 6,170,018 B1 | 1/2001 | Voll et al. |
| 6,171,239 B1 | 1/2001 | Humphrey |
| 6,173,260 B1 | 1/2001 | Slaney |
| 6,175,753 B1 | 1/2001 | Menkes et al. |
| 6,182,113 B1 | 1/2001 | Narayanaswami |
| 6,190,314 B1 | 2/2001 | Ark et al. |
| 6,212,502 B1 | 4/2001 | Ball et al. |
| 6,228,038 B1 | 5/2001 | Claessens |
| 6,236,885 B1 | 5/2001 | Hunter et al. |
| 6,236,975 B1 | 5/2001 | Boe et al. |
| 6,254,536 B1 | 7/2001 | DeVito |
| 6,280,198 B1 | 8/2001 | Calhoun et al. |
| 6,286,005 B1 | 9/2001 | Cannon |
| 6,289,234 B1 | 9/2001 | Mueller |
| 6,292,688 B1 | 9/2001 | Patton |
| 6,299,308 B1 | 10/2001 | Voronka et al. |
| 6,301,493 B1 | 10/2001 | Marro et al. |

(56) References Cited

U.S. PATENT DOCUMENTS

| | | |
|---|---|---|
| 6,315,569 B1 | 11/2001 | Zaltman |
| 6,330,470 B1 | 12/2001 | Tucker et al. |
| 6,334,778 B1 | 1/2002 | Brown |
| 6,358,201 B1 | 3/2002 | Childre et al. |
| 6,370,513 B1 | 4/2002 | Kolawa et al. |
| 6,374,143 B1 | 4/2002 | Berrang et al. |
| 6,381,481 B1 | 4/2002 | Levendowski et al. |
| 6,398,643 B1 | 6/2002 | Knowles et al. |
| 6,422,999 B1 | 7/2002 | Hill |
| 6,434,419 B1 | 8/2002 | Gevins et al. |
| 6,435,878 B1 | 8/2002 | Reynolds et al. |
| 6,453,194 B1 | 9/2002 | Hill |
| 6,453,241 B1 | 9/2002 | Bassett, Jr. et al. |
| 6,487,444 B2 | 11/2002 | Mimura |
| 6,488,617 B1 | 12/2002 | Katz |
| 6,510,340 B1 | 1/2003 | Jordan |
| 6,520,905 B1 | 2/2003 | Surve et al. |
| 6,545,685 B1 | 4/2003 | Dorbie |
| 6,575,902 B1 | 6/2003 | Burton |
| 6,577,329 B1 | 6/2003 | Flickner et al. |
| 6,585,521 B1 | 7/2003 | Obrador |
| 6,594,521 B2 | 7/2003 | Tucker |
| 6,598,006 B1 | 7/2003 | Honda et al. |
| 6,609,024 B1 | 8/2003 | Ryu et al. |
| 6,648,822 B2 | 11/2003 | Hamamoto et al. |
| 6,652,283 B1 | 11/2003 | Van Schaack et al. |
| 6,654,626 B2 | 11/2003 | Devlin et al. |
| 6,662,052 B1 | 12/2003 | Sarwal et al. |
| 6,665,560 B2 | 12/2003 | Becker et al. |
| 6,678,685 B2 | 1/2004 | McGill et al. |
| 6,688,890 B2 | 2/2004 | von Buegner |
| 6,708,051 B1 | 3/2004 | Durousseau |
| 6,712,468 B1 | 3/2004 | Edwards |
| 6,754,524 B2 | 6/2004 | Johnson, Jr. |
| 6,757,556 B2 | 6/2004 | Gopinathan et al. |
| 6,788,882 B1 | 9/2004 | Geer et al. |
| 6,792,304 B1 | 9/2004 | Silberstein |
| 6,842,877 B2 | 1/2005 | Robarts et al. |
| 6,850,252 B1 | 2/2005 | Hoffberg |
| 6,852,875 B2 | 2/2005 | Prakash |
| 6,888,457 B2 | 5/2005 | Wilkinson et al. |
| 6,904,408 B1 | 6/2005 | McCarthy et al. |
| 6,950,698 B2 | 9/2005 | Sarkela et al. |
| 6,958,710 B2 | 10/2005 | Zhang et al. |
| 6,973,342 B1 | 12/2005 | Swanson |
| 6,993,380 B1 | 1/2006 | Modarres |
| 7,020,508 B2 | 3/2006 | Stivoric et al. |
| 7,043,056 B2 | 5/2006 | Edwards et al. |
| 7,047,550 B1 | 5/2006 | Yasukawa et al. |
| 7,113,916 B1 | 9/2006 | Hill |
| 7,120,880 B1 | 10/2006 | Dryer et al. |
| 7,130,673 B2 | 10/2006 | Tolvanen-Laakso et al. |
| 7,150,715 B2 | 12/2006 | Collura et al. |
| 7,164,967 B2 | 1/2007 | Etienne-Cummings et al. |
| 7,177,675 B2 | 2/2007 | Suffin et al. |
| 7,222,071 B2 | 5/2007 | Neuhauser et al. |
| 7,246,081 B2 | 7/2007 | Hill |
| 7,249,708 B2 | 7/2007 | McConnell et al. |
| 7,269,590 B2 | 9/2007 | Hull et al. |
| 7,272,982 B2 | 9/2007 | Neuhauser et al. |
| 7,286,871 B2 | 10/2007 | Cohen |
| 7,340,060 B2 | 3/2008 | Tomkins et al. |
| 7,359,894 B1 | 4/2008 | Liebman et al. |
| 7,391,835 B1 | 6/2008 | Gross et al. |
| 7,394,385 B2 | 7/2008 | Franco, Jr. et al. |
| 7,408,460 B2 | 8/2008 | Crystal et al. |
| 7,420,464 B2 | 9/2008 | Fitzgerald et al. |
| 7,443,292 B2 | 10/2008 | Jensen et al. |
| 7,460,827 B2 | 12/2008 | Schuster et al. |
| 7,463,143 B2 | 12/2008 | Forr et al. |
| 7,463,144 B2 | 12/2008 | Crystal et al. |
| 7,471,987 B2 | 12/2008 | Crystal et al. |
| 7,483,835 B2 | 1/2009 | Neuhauser et al. |
| 7,483,844 B2 | 1/2009 | Takakura et al. |
| 7,496,400 B2 | 2/2009 | Hoskonen et al. |
| 7,548,774 B2 | 6/2009 | Kurtz et al. |
| 7,551,952 B2 | 6/2009 | Gevins et al. |
| 7,592,908 B2 | 9/2009 | Zhang et al. |
| 7,614,066 B2 | 11/2009 | Urdang et al. |
| 7,623,823 B2 | 11/2009 | Zito et al. |
| 7,630,757 B2 | 12/2009 | Dorfmeister et al. |
| 7,636,456 B2 | 12/2009 | Collins et al. |
| 7,650,793 B2 | 1/2010 | Jensen et al. |
| 7,657,523 B2 | 2/2010 | Ebanks |
| 7,658,327 B2 | 2/2010 | Tuchman et al. |
| 7,689,272 B2 | 3/2010 | Farwell |
| 7,697,979 B2 | 4/2010 | Martinerie et al. |
| 7,698,238 B2 | 4/2010 | Barletta et al. |
| 7,720,351 B2 | 5/2010 | Levitan |
| 7,729,755 B2 | 6/2010 | Laken |
| 7,765,564 B2 | 7/2010 | Deng |
| 7,774,052 B2 | 8/2010 | Burton et al. |
| 7,781,548 B2 | 8/2010 | Fitzgerald et al. |
| 7,797,186 B2 | 9/2010 | Dybus |
| 7,809,420 B2 | 10/2010 | Hannula et al. |
| 7,816,951 B1 | 10/2010 | Lee |
| 7,840,248 B2 | 11/2010 | Fuchs et al. |
| 7,840,250 B2 | 11/2010 | Tucker |
| 7,844,484 B2 | 11/2010 | Arnett et al. |
| 7,865,235 B2 | 1/2011 | Le et al. |
| 7,865,394 B1 | 1/2011 | Calloway |
| 7,892,764 B2 | 2/2011 | Xiong et al. |
| 7,895,075 B2 | 2/2011 | Gettys et al. |
| 7,895,625 B1 | 2/2011 | Bryan et al. |
| 7,908,133 B2 | 3/2011 | Neuhauser |
| 7,917,366 B1 | 3/2011 | Levanon et al. |
| 7,930,199 B1 | 4/2011 | Hill |
| 7,946,974 B2 | 5/2011 | Lordereau |
| 7,962,315 B2 | 6/2011 | Jensen et al. |
| 7,974,889 B2 | 7/2011 | Raimbeault |
| 7,988,557 B2 | 8/2011 | Soderlund |
| 8,014,847 B2 | 9/2011 | Shastri et al. |
| 8,027,518 B2 | 9/2011 | Baker et al. |
| 8,055,722 B2 | 11/2011 | Hille |
| 8,060,795 B2 | 11/2011 | Bakekolo et al. |
| 8,065,203 B1 | 11/2011 | Chien et al. |
| 8,069,125 B2 | 11/2011 | Jung et al. |
| 8,073,707 B2 | 12/2011 | Teller et al. |
| 8,079,054 B1 | 12/2011 | Dhawan et al. |
| 8,082,215 B2 | 12/2011 | Jung et al. |
| 8,086,563 B2 | 12/2011 | Jung et al. |
| 8,098,152 B2 | 1/2012 | Zhang et al. |
| 8,099,159 B2 | 1/2012 | Cook |
| 8,099,315 B2 | 1/2012 | Amento et al. |
| 8,103,328 B2 | 1/2012 | Turner et al. |
| 8,126,220 B2 | 2/2012 | Greig |
| 8,135,606 B2 | 3/2012 | Dupree |
| 8,151,298 B2 | 4/2012 | Begeja et al. |
| 8,165,916 B2 | 4/2012 | Hoffberg et al. |
| 8,179,604 B1 | 5/2012 | Prada Gomez et al. |
| 8,196,168 B1 | 6/2012 | Bryan et al. |
| 8,200,775 B2 | 6/2012 | Moore |
| 8,209,224 B2 | 6/2012 | Pradeep et al. |
| 8,229,469 B2 | 7/2012 | Zhang et al. |
| 8,235,725 B1 | 8/2012 | Hill |
| 8,239,030 B1 | 8/2012 | Hagedorn et al. |
| 8,255,267 B2 | 8/2012 | Breiter |
| 8,270,814 B2 | 9/2012 | Pradeep et al. |
| 8,296,172 B2 | 10/2012 | Marci et al. |
| 8,300,526 B2 | 10/2012 | Saito et al. |
| 8,308,562 B2 | 11/2012 | Patton |
| 8,326,002 B2 | 12/2012 | Hill |
| 8,327,395 B2 | 12/2012 | Lee |
| 8,332,883 B2 | 12/2012 | Lee |
| 8,335,715 B2 | 12/2012 | Pradeep et al. |
| 8,381,244 B2 | 2/2013 | King et al. |
| 8,386,312 B2 | 2/2013 | Pradeep et al. |
| 8,386,313 B2 | 2/2013 | Pradeep et al. |
| 8,388,165 B2 | 3/2013 | Zhang |
| 8,392,250 B2 | 3/2013 | Pradeep et al. |
| 8,392,251 B2 | 3/2013 | Pradeep et al. |
| 8,392,253 B2 | 3/2013 | Pradeep et al. |
| 8,392,254 B2 | 3/2013 | Pradeep et al. |
| 8,392,255 B2 | 3/2013 | Pradeep et al. |

(56) References Cited

U.S. PATENT DOCUMENTS

| | | |
|---|---|---|
| 8,396,744 B2 | 3/2013 | Pradeep et al. |
| 8,442,429 B2 | 5/2013 | Hawit |
| 8,464,288 B2 | 6/2013 | Pradeep et al. |
| 8,467,133 B2 | 6/2013 | Miller |
| 8,473,345 B2 | 6/2013 | Pradeep et al. |
| 8,477,425 B2 | 7/2013 | Border et al. |
| 8,484,081 B2 | 7/2013 | Pradeep et al. |
| 8,494,610 B2 | 7/2013 | Pradeep et al. |
| 8,494,905 B2 | 7/2013 | Pradeep et al. |
| 8,533,042 B2 | 9/2013 | Pradeep et al. |
| 8,543,446 B2 | 9/2013 | Richardson et al. |
| 8,548,852 B2 | 10/2013 | Pradeep et al. |
| 8,560,530 B2 | 10/2013 | Krichman et al. |
| 8,561,095 B2 | 10/2013 | Dimitrova et al. |
| 8,600,100 B2 | 12/2013 | Hill |
| 8,635,105 B2 | 1/2014 | Pradeep et al. |
| 8,655,428 B2 | 2/2014 | Pradeep et al. |
| 8,655,437 B2 | 2/2014 | Pradeep et al. |
| 8,684,742 B2 | 4/2014 | Siefert |
| 8,700,009 B2 | 4/2014 | Quy |
| 8,762,202 B2 | 6/2014 | Pradeep et al. |
| 8,764,652 B2 | 7/2014 | Lee et al. |
| 8,788,372 B2 | 7/2014 | Kettner et al. |
| 8,793,715 B1 | 7/2014 | Weitzenfeld et al. |
| 8,793,727 B2 | 7/2014 | Serdiuk |
| 8,856,235 B2 | 10/2014 | Zhou et al. |
| 8,874,727 B2 | 10/2014 | Swahar |
| 9,000,927 B2 * | 4/2015 | Xiong ............... G06Q 30/0269 340/5.82 |
| 9,021,515 B2 | 4/2015 | Lee et al. |
| 9,032,110 B2 * | 5/2015 | Frank .................... G06F 17/28 710/14 |
| 9,336,535 B2 | 5/2016 | Pradeep et al. |
| 9,514,436 B2 | 12/2016 | Marci et al. |
| 9,514,439 B2 | 12/2016 | Marci et al. |
| 9,521,960 B2 | 12/2016 | Lee et al. |
| 9,557,814 B2 | 1/2017 | Weising |
| 9,560,984 B2 | 2/2017 | Pradeep et al. |
| 2001/0013009 A1 | 8/2001 | Greening et al. |
| 2001/0020236 A1 | 9/2001 | Cannon |
| 2001/0029468 A1 | 10/2001 | Yamaguchi et al. |
| 2001/0032140 A1 | 10/2001 | Hoffman |
| 2001/0056225 A1 | 12/2001 | DeVito |
| 2002/0053076 A1 | 5/2002 | Landesmann |
| 2002/0055857 A1 | 5/2002 | Mault |
| 2002/0056087 A1 | 5/2002 | Berezowski et al. |
| 2002/0056124 A1 | 5/2002 | Hay |
| 2002/0059577 A1 | 5/2002 | Lu et al. |
| 2002/0065826 A1 | 5/2002 | Bell et al. |
| 2002/0072952 A1 | 6/2002 | Hamzey et al. |
| 2002/0077534 A1 | 6/2002 | DuRousseau |
| 2002/0082902 A1 | 6/2002 | Ando et al. |
| 2002/0103429 A1 | 8/2002 | deCharms |
| 2002/0111796 A1 | 8/2002 | Nemoto |
| 2002/0143627 A1 | 10/2002 | Barsade et al. |
| 2002/0155878 A1 | 10/2002 | Lert, Jr. et al. |
| 2002/0156842 A1 | 10/2002 | Signes et al. |
| 2002/0169665 A1 | 11/2002 | Hughes et al. |
| 2002/0188216 A1 | 12/2002 | Kayyali et al. |
| 2002/0188217 A1 | 12/2002 | Farwell |
| 2002/0193670 A1 | 12/2002 | Garfield et al. |
| 2003/0013981 A1 | 1/2003 | Gevins et al. |
| 2003/0036955 A1 | 2/2003 | Tanaka et al. |
| 2003/0037333 A1 | 2/2003 | Ghashghai et al. |
| 2003/0044050 A1 | 3/2003 | Clark et al. |
| 2003/0059750 A1 | 3/2003 | Bindler et al. |
| 2003/0063222 A1 | 4/2003 | Creed et al. |
| 2003/0065524 A1 | 4/2003 | Giacchetti et al. |
| 2003/0073921 A1 | 4/2003 | Sohmer et al. |
| 2003/0081834 A1 | 5/2003 | Philomin et al. |
| 2003/0093784 A1 * | 5/2003 | Dimitrova ............. H04N 7/163 725/10 |
| 2003/0093792 A1 | 5/2003 | Labeeb et al. |
| 2003/0100998 A2 | 5/2003 | Brunner et al. |
| 2003/0104865 A1 | 6/2003 | Itkis et al. |
| 2003/0131351 A1 | 7/2003 | Shapira |
| 2003/0149344 A1 | 8/2003 | Nizan |
| 2003/0165270 A1 | 9/2003 | Endrikhovski et al. |
| 2003/0177488 A1 | 9/2003 | Smith et al. |
| 2003/0204412 A1 | 10/2003 | Brier |
| 2003/0208754 A1 | 11/2003 | Sridhar et al. |
| 2003/0233278 A1 | 12/2003 | Marshall |
| 2004/0001616 A1 | 1/2004 | Gutta et al. |
| 2004/0005143 A1 | 1/2004 | Tsuru et al. |
| 2004/0013398 A1 | 1/2004 | Miura et al. |
| 2004/0015608 A1 | 1/2004 | Ellis et al. |
| 2004/0055448 A1 | 3/2004 | Byon |
| 2004/0068431 A1 | 4/2004 | Smith et al. |
| 2004/0073129 A1 | 4/2004 | Caldwell et al. |
| 2004/0092809 A1 | 5/2004 | DeCharms |
| 2004/0098298 A1 | 5/2004 | Yin |
| 2004/0101212 A1 | 5/2004 | Fedorovskaya et al. |
| 2004/0133081 A1 | 7/2004 | Teller et al. |
| 2004/0187167 A1 | 9/2004 | Maguire et al. |
| 2004/0193068 A1 | 9/2004 | Burton et al. |
| 2004/0210159 A1 | 10/2004 | Kibar |
| 2004/0219184 A1 | 11/2004 | Brown et al. |
| 2004/0220483 A1 | 11/2004 | Yeo et al. |
| 2004/0236623 A1 | 11/2004 | Gopalakrishnan |
| 2005/0010475 A1 | 1/2005 | Perkowski et al. |
| 2005/0041951 A1 | 2/2005 | Inoue et al. |
| 2005/0043646 A1 | 2/2005 | Viirre et al. |
| 2005/0060312 A1 | 3/2005 | Curtiss et al. |
| 2005/0062637 A1 | 3/2005 | El Zabadani et al. |
| 2005/0071462 A1 | 3/2005 | Bodin et al. |
| 2005/0071865 A1 | 3/2005 | Martins |
| 2005/0076359 A1 | 4/2005 | Pierson et al. |
| 2005/0079474 A1 | 4/2005 | Lowe |
| 2005/0097594 A1 | 5/2005 | O'Donnell et al. |
| 2005/0107716 A1 | 5/2005 | Eaton et al. |
| 2005/0113649 A1 | 5/2005 | Bergantino |
| 2005/0132401 A1 | 6/2005 | Boccon-Gibod et al. |
| 2005/0143629 A1 | 6/2005 | Farwell |
| 2005/0149964 A1 | 7/2005 | Thomas et al. |
| 2005/0154290 A1 | 7/2005 | Langleben |
| 2005/0165766 A1 | 7/2005 | Szabo |
| 2005/0177058 A1 | 8/2005 | Sobell |
| 2005/0197590 A1 | 9/2005 | Osorio et al. |
| 2005/0203798 A1 | 9/2005 | Jensen et al. |
| 2005/0216243 A1 | 9/2005 | Graham et al. |
| 2005/0223237 A1 | 10/2005 | Barletta et al. |
| 2005/0227233 A1 | 10/2005 | Buxton et al. |
| 2005/0240956 A1 | 10/2005 | Smith et al. |
| 2005/0256905 A1 | 11/2005 | Gruhl et al. |
| 2005/0261980 A1 | 11/2005 | Hadi |
| 2005/0267798 A1 | 12/2005 | Panara |
| 2005/0272017 A1 | 12/2005 | Neuhauser et al. |
| 2005/0273017 A1 | 12/2005 | Gordon |
| 2005/0273802 A1 | 12/2005 | Crystal et al. |
| 2005/0288954 A1 | 12/2005 | McCarthy et al. |
| 2005/0289582 A1 | 12/2005 | Tavares et al. |
| 2006/0003732 A1 | 1/2006 | Neuhauser et al. |
| 2006/0009702 A1 | 1/2006 | Iwaki et al. |
| 2006/0010470 A1 | 1/2006 | Kurosaki et al. |
| 2006/0035707 A1 | 2/2006 | Nguyen et al. |
| 2006/0041548 A1 | 2/2006 | Parsons et al. |
| 2006/0042483 A1 | 3/2006 | Work et al. |
| 2006/0053110 A1 | 3/2006 | McDonald et al. |
| 2006/0069663 A1 | 3/2006 | Adar et al. |
| 2006/0075003 A1 | 4/2006 | Adams et al. |
| 2006/0093998 A1 | 5/2006 | Vertegaal |
| 2006/0111044 A1 | 5/2006 | Keller |
| 2006/0111644 A1 | 5/2006 | Guttag et al. |
| 2006/0129458 A1 | 6/2006 | Maggio |
| 2006/0149337 A1 | 7/2006 | John |
| 2006/0167376 A1 | 7/2006 | Viirre et al. |
| 2006/0168613 A1 | 7/2006 | Wood et al. |
| 2006/0168630 A1 | 7/2006 | Davies |
| 2006/0176289 A1 | 8/2006 | Horn |
| 2006/0190822 A1 | 8/2006 | Basson et al. |
| 2006/0218046 A1 | 9/2006 | Carfi et al. |
| 2006/0256133 A1 | 11/2006 | Rosenberg |
| 2006/0257834 A1 | 11/2006 | Lee et al. |
| 2006/0259360 A1 | 11/2006 | Flinn et al. |

(56) References Cited

U.S. PATENT DOCUMENTS

| | | |
|---|---|---|
| 2006/0259371 A1 | 11/2006 | Perrier et al. |
| 2006/0293921 A1 | 12/2006 | McCarthy et al. |
| 2007/0016096 A1 | 1/2007 | McNabb |
| 2007/0038516 A1 | 2/2007 | Apple et al. |
| 2007/0048707 A1 | 3/2007 | Caamano et al. |
| 2007/0050256 A1 | 3/2007 | Walker et al. |
| 2007/0055169 A1 | 3/2007 | Lee et al. |
| 2007/0060830 A1 | 3/2007 | Le et al. |
| 2007/0060831 A1 | 3/2007 | Le et al. |
| 2007/0061720 A1 | 3/2007 | Kriger |
| 2007/0066874 A1 | 3/2007 | Cook |
| 2007/0066915 A1 | 3/2007 | Frei et al. |
| 2007/0066916 A1 | 3/2007 | Lemos |
| 2007/0067007 A1 | 3/2007 | Schulman et al. |
| 2007/0067305 A1 | 3/2007 | Ives |
| 2007/0078700 A1 | 4/2007 | Lenzmann et al. |
| 2007/0078706 A1 | 4/2007 | Datta et al. |
| 2007/0079331 A1 | 4/2007 | Datta et al. |
| 2007/0101360 A1 | 5/2007 | Gutta et al. |
| 2007/0106170 A1 | 5/2007 | Dunseath, Jr. et al. |
| 2007/0112460 A1 | 5/2007 | Kiselik |
| 2007/0135727 A1 | 6/2007 | Virtanen et al. |
| 2007/0135728 A1 | 6/2007 | Snyder et al. |
| 2007/0136753 A1 | 6/2007 | Bovenschulte et al. |
| 2007/0150916 A1 | 6/2007 | Begole et al. |
| 2007/0173733 A1 | 7/2007 | Le et al. |
| 2007/0198510 A1 | 8/2007 | Ebanks |
| 2007/0209047 A1 | 9/2007 | Hallberg et al. |
| 2007/0214121 A1 | 9/2007 | Ebanks |
| 2007/0214471 A1 | 9/2007 | Rosenberg |
| 2007/0225585 A1 | 9/2007 | Washbon et al. |
| 2007/0225674 A1 | 9/2007 | Molnar et al. |
| 2007/0226760 A1 | 9/2007 | Neuhauser et al. |
| 2007/0235716 A1 | 10/2007 | Delic et al. |
| 2007/0238945 A1 | 10/2007 | Delic et al. |
| 2007/0239713 A1 | 10/2007 | Leblang et al. |
| 2007/0250846 A1 | 10/2007 | Swix et al. |
| 2007/0250901 A1 | 10/2007 | McIntire et al. |
| 2007/0265507 A1 | 11/2007 | de Lemos |
| 2007/0282566 A1 | 12/2007 | Whitlow et al. |
| 2007/0294132 A1 | 12/2007 | Zhang et al. |
| 2007/0294705 A1 | 12/2007 | Gopalakrishnan |
| 2007/0294706 A1 | 12/2007 | Neuhauser et al. |
| 2008/0001600 A1 | 1/2008 | deCharms |
| 2008/0004940 A1 | 1/2008 | Rolleston Phillips |
| 2008/0010110 A1 | 1/2008 | Neuhauser et al. |
| 2008/0027345 A1 | 1/2008 | Kumada et al. |
| 2008/0040740 A1 | 2/2008 | Plotnick et al. |
| 2008/0059997 A1 | 3/2008 | Plotnick et al. |
| 2008/0065468 A1 | 3/2008 | Berg et al. |
| 2008/0065721 A1 | 3/2008 | Cragun |
| 2008/0081961 A1 | 4/2008 | Westbrook et al. |
| 2008/0082019 A1 | 4/2008 | Ludving et al. |
| 2008/0086356 A1 | 4/2008 | Glassman et al. |
| 2008/0091463 A1 | 4/2008 | Shakamuri |
| 2008/0091512 A1 | 4/2008 | Marci et al. |
| 2008/0097854 A1 | 4/2008 | Young |
| 2008/0109840 A1 | 5/2008 | Walter et al. |
| 2008/0125110 A1 | 5/2008 | Ritter |
| 2008/0133724 A1 | 6/2008 | Clark |
| 2008/0147488 A1 | 6/2008 | Tunick et al. |
| 2008/0147742 A1 | 6/2008 | Allen |
| 2008/0152300 A1 | 6/2008 | Knee et al. |
| 2008/0162182 A1 | 7/2008 | Cazares et al. |
| 2008/0177197 A1 | 7/2008 | Lee et al. |
| 2008/0195471 A1 | 8/2008 | Dube et al. |
| 2008/0204273 A1 | 8/2008 | Crystal et al. |
| 2008/0208072 A1 | 8/2008 | Fadem et al. |
| 2008/0214902 A1 | 9/2008 | Lee et al. |
| 2008/0218472 A1 | 9/2008 | Breen et al. |
| 2008/0221400 A1 | 9/2008 | Lee et al. |
| 2008/0221472 A1 | 9/2008 | Lee et al. |
| 2008/0221969 A1 | 9/2008 | Lee et al. |
| 2008/0222670 A1 | 9/2008 | Lee et al. |
| 2008/0222671 A1 | 9/2008 | Lee et al. |
| 2008/0228077 A1 | 9/2008 | Wilk et al. |
| 2008/0249865 A1 | 10/2008 | Angell et al. |
| 2008/0255949 A1 | 10/2008 | Genco et al. |
| 2008/0287821 A1 | 11/2008 | Jung et al. |
| 2008/0295126 A1 | 11/2008 | Lee et al. |
| 2008/0306398 A1 | 12/2008 | Uchiyama et al. |
| 2009/0018996 A1 | 1/2009 | Hunt et al. |
| 2009/0024049 A1 | 1/2009 | Pradeep et al. |
| 2009/0024447 A1 | 1/2009 | Pradeep et al. |
| 2009/0024448 A1 | 1/2009 | Pradeep et al. |
| 2009/0024449 A1 | 1/2009 | Pradeep et al. |
| 2009/0024475 A1 | 1/2009 | Pradeep et al. |
| 2009/0024747 A1 | 1/2009 | Moses et al. |
| 2009/0025023 A1 | 1/2009 | Pradeep et al. |
| 2009/0025024 A1 | 1/2009 | Beser et al. |
| 2009/0030287 A1 | 1/2009 | Pradeep et al. |
| 2009/0030303 A1 | 1/2009 | Pradeep et al. |
| 2009/0030717 A1 | 1/2009 | Pradeep et al. |
| 2009/0030762 A1 | 1/2009 | Lee et al. |
| 2009/0030780 A1 | 1/2009 | York et al. |
| 2009/0030930 A1 | 1/2009 | Pradeep et al. |
| 2009/0036755 A1 | 2/2009 | Pradeep et al. |
| 2009/0036756 A1 | 2/2009 | Pradeep et al. |
| 2009/0037575 A1 | 2/2009 | Crystal et al. |
| 2009/0060240 A1 | 3/2009 | Coughlan et al. |
| 2009/0062629 A1 | 3/2009 | Pradeep et al. |
| 2009/0062679 A1 | 3/2009 | Tan et al. |
| 2009/0062680 A1 | 3/2009 | Sandford |
| 2009/0062681 A1 | 3/2009 | Pradeep et al. |
| 2009/0063255 A1 | 3/2009 | Pradeep et al. |
| 2009/0063256 A1 | 3/2009 | Pradeep et al. |
| 2009/0066722 A1 | 3/2009 | Kriger et al. |
| 2009/0069652 A1 | 3/2009 | Lee et al. |
| 2009/0070219 A1 | 3/2009 | D'Angelo et al. |
| 2009/0070798 A1 | 3/2009 | Lee et al. |
| 2009/0082643 A1 | 3/2009 | Pradeep et al. |
| 2009/0082689 A1 | 3/2009 | Guttag et al. |
| 2009/0082692 A1 | 3/2009 | Hale et al. |
| 2009/0083129 A1 | 3/2009 | Pradeep et al. |
| 2009/0088610 A1 | 4/2009 | Lee et al. |
| 2009/0089830 A1 | 4/2009 | Chandratillake et al. |
| 2009/0094286 A1 | 4/2009 | Lee et al. |
| 2009/0094627 A1 | 4/2009 | Lee et al. |
| 2009/0094628 A1 | 4/2009 | Lee et al. |
| 2009/0094629 A1 | 4/2009 | Lee et al. |
| 2009/0097689 A1 | 4/2009 | Prest et al. |
| 2009/0099873 A1 | 4/2009 | Kurple |
| 2009/0112077 A1 | 4/2009 | Nguyen et al. |
| 2009/0112117 A1 | 4/2009 | Rewari |
| 2009/0119154 A1 | 5/2009 | Jung et al. |
| 2009/0131764 A1 | 5/2009 | Lee et al. |
| 2009/0132441 A1 | 5/2009 | Muller et al. |
| 2009/0133047 A1 | 5/2009 | Lee et al. |
| 2009/0138356 A1 | 5/2009 | Pomplun |
| 2009/0144780 A1 | 6/2009 | Toebes et al. |
| 2009/0150919 A1 | 6/2009 | Lee et al. |
| 2009/0150920 A1 | 6/2009 | Jones |
| 2009/0153328 A1 | 6/2009 | Otani et al. |
| 2009/0156907 A1 | 6/2009 | Jung et al. |
| 2009/0156955 A1 | 6/2009 | Jung et al. |
| 2009/0158308 A1 | 6/2009 | Weitzenfeld et al. |
| 2009/0163777 A1 | 6/2009 | Jung et al. |
| 2009/0164132 A1 | 6/2009 | Jung et al. |
| 2009/0171164 A1 | 7/2009 | Jung et al. |
| 2009/0183193 A1* | 7/2009 | Miller, IV ............... G06F 3/017 725/10 |
| 2009/0187467 A1 | 7/2009 | Fang et al. |
| 2009/0195392 A1 | 8/2009 | Zalewski |
| 2009/0214060 A1 | 8/2009 | Chuang et al. |
| 2009/0216611 A1 | 8/2009 | Leonard et al. |
| 2009/0221928 A1 | 9/2009 | Einav et al. |
| 2009/0248484 A1 | 10/2009 | Surendran et al. |
| 2009/0248496 A1 | 10/2009 | Hueter et al. |
| 2009/0248594 A1 | 10/2009 | Castleman et al. |
| 2009/0249223 A1 | 10/2009 | Barsook et al. |
| 2009/0253996 A1 | 10/2009 | Lee et al. |
| 2009/0259137 A1 | 10/2009 | Delic et al. |
| 2009/0259509 A1 | 10/2009 | Landvater |
| 2009/0271294 A1 | 10/2009 | Hadi |

(56) References Cited

U.S. PATENT DOCUMENTS

| | | |
|---|---|---|
| 2009/0280215 A1 | 11/2009 | Yotsumoto |
| 2009/0287108 A1 | 11/2009 | Levy |
| 2009/0292587 A1 | 11/2009 | Fitzgerald |
| 2009/0300672 A1 | 12/2009 | Van Gulik |
| 2009/0305006 A1 | 12/2009 | Steffen |
| 2009/0318773 A1 | 12/2009 | Jung et al. |
| 2009/0318826 A1 | 12/2009 | Green et al. |
| 2009/0327068 A1 | 12/2009 | Pradeep et al. |
| 2009/0327907 A1 | 12/2009 | Estrada et al. |
| 2009/0328089 A1 | 12/2009 | Pradeep et al. |
| 2009/0328122 A1 | 12/2009 | Amento et al. |
| 2010/0004977 A1 | 1/2010 | Marci et al. |
| 2010/0010370 A1* | 1/2010 | De Lemos ............ A61B 3/112 600/558 |
| 2010/0022821 A1 | 1/2010 | Dubi et al. |
| 2010/0039618 A1 | 2/2010 | De Lemos |
| 2010/0041962 A1 | 2/2010 | Causevic et al. |
| 2010/0042012 A1 | 2/2010 | Alhussiny |
| 2010/0060300 A1 | 3/2010 | Muller et al. |
| 2010/0094702 A1 | 4/2010 | Silberstein |
| 2010/0094869 A1 | 4/2010 | Ebanks |
| 2010/0121716 A1 | 5/2010 | Golan |
| 2010/0125219 A1 | 5/2010 | Harris et al. |
| 2010/0145176 A1 | 6/2010 | Himes |
| 2010/0145215 A1 | 6/2010 | Pradeep et al. |
| 2010/0145217 A1 | 6/2010 | Otto et al. |
| 2010/0153175 A1 | 6/2010 | Pearson et al. |
| 2010/0169153 A1 | 7/2010 | Hwacinski et al. |
| 2010/0169162 A1 | 7/2010 | Anderson et al. |
| 2010/0179881 A1 | 7/2010 | Wiederstein |
| 2010/0180029 A1 | 7/2010 | Fourman |
| 2010/0183279 A1 | 7/2010 | Pradeep et al. |
| 2010/0186031 A1 | 7/2010 | Pradeep et al. |
| 2010/0186032 A1 | 7/2010 | Pradeep et al. |
| 2010/0198042 A1 | 8/2010 | Popescu et al. |
| 2010/0211439 A1* | 8/2010 | Marci .................... G06Q 10/10 705/7.29 |
| 2010/0214318 A1 | 8/2010 | Pradeep et al. |
| 2010/0215289 A1 | 8/2010 | Pradeep et al. |
| 2010/0218208 A1 | 8/2010 | Holden |
| 2010/0223094 A1 | 9/2010 | Cumming et al. |
| 2010/0228604 A1 | 9/2010 | Desai et al. |
| 2010/0228614 A1 | 9/2010 | Zhang et al. |
| 2010/0234752 A1 | 9/2010 | Sullivan et al. |
| 2010/0241580 A1 | 9/2010 | Schleier-Smith |
| 2010/0249538 A1 | 9/2010 | Pradeep et al. |
| 2010/0249636 A1 | 9/2010 | Pradeep et al. |
| 2010/0250325 A1 | 9/2010 | Pradeep et al. |
| 2010/0250347 A1 | 9/2010 | Rainier et al. |
| 2010/0250458 A1 | 9/2010 | Ho |
| 2010/0257023 A1 | 10/2010 | Kendall et al. |
| 2010/0257052 A1 | 10/2010 | Zito et al. |
| 2010/0262477 A1 | 10/2010 | Hillerbrand et al. |
| 2010/0263005 A1 | 10/2010 | White |
| 2010/0268540 A1 | 10/2010 | Arshi et al. |
| 2010/0268573 A1 | 10/2010 | Jain et al. |
| 2010/0268720 A1 | 10/2010 | Spivack et al. |
| 2010/0269127 A1 | 10/2010 | Krug |
| 2010/0274152 A1 | 10/2010 | McPeck et al. |
| 2010/0274153 A1 | 10/2010 | Tucker et al. |
| 2010/0287152 A1 | 11/2010 | Hauser |
| 2010/0292998 A1 | 11/2010 | Bodlaender et al. |
| 2010/0306030 A1 | 12/2010 | Mawani |
| 2010/0306120 A1 | 12/2010 | Ciptawilangga |
| 2010/0317988 A1 | 12/2010 | Terada et al. |
| 2010/0318507 A1 | 12/2010 | Grant et al. |
| 2010/0325660 A1 | 12/2010 | Holden |
| 2010/0331661 A1 | 12/2010 | Nakagawa |
| 2010/0332283 A1 | 12/2010 | Ng et al. |
| 2011/0004089 A1 | 1/2011 | Chou |
| 2011/0015503 A1 | 1/2011 | Joffe et al. |
| 2011/0020778 A1 | 1/2011 | Forbes |
| 2011/0022965 A1 | 1/2011 | Lawrence et al. |
| 2011/0040155 A1 | 2/2011 | Guzak et al. |
| 2011/0040202 A1 | 2/2011 | Luo et al. |
| 2011/0043759 A1 | 2/2011 | Bushinsky |
| 2011/0046473 A1 | 2/2011 | Pradeep et al. |
| 2011/0046502 A1 | 2/2011 | Pradeep et al. |
| 2011/0046503 A1 | 2/2011 | Pradeep et al. |
| 2011/0046504 A1 | 2/2011 | Pradeep et al. |
| 2011/0047035 A1 | 2/2011 | Gidwani et al. |
| 2011/0047121 A1 | 2/2011 | Pradeep et al. |
| 2011/0059422 A1 | 3/2011 | Masaoka |
| 2011/0071874 A1 | 3/2011 | Schneersohn et al. |
| 2011/0076942 A1 | 3/2011 | Taveau et al. |
| 2011/0084795 A1 | 4/2011 | Fukuyori |
| 2011/0085700 A1 | 4/2011 | Lee |
| 2011/0098593 A1 | 4/2011 | Low et al. |
| 2011/0105937 A1 | 5/2011 | Pradeep et al. |
| 2011/0106621 A1 | 5/2011 | Pradeep et al. |
| 2011/0106750 A1 | 5/2011 | Pradeep et al. |
| 2011/0119124 A1 | 5/2011 | Pradeep et al. |
| 2011/0119129 A1 | 5/2011 | Pradeep et al. |
| 2011/0119130 A1 | 5/2011 | Agan et al. |
| 2011/0124977 A1 | 5/2011 | Winarski |
| 2011/0131274 A1 | 6/2011 | Hille |
| 2011/0137894 A1 | 6/2011 | Narayanan et al. |
| 2011/0138326 A1 | 6/2011 | Roberts et al. |
| 2011/0144519 A1 | 6/2011 | Causevic |
| 2011/0153390 A1 | 6/2011 | Harris |
| 2011/0153391 A1 | 6/2011 | Tenbrock |
| 2011/0153414 A1 | 6/2011 | Elvekrog et al. |
| 2011/0153423 A1 | 6/2011 | Elvekrog et al. |
| 2011/0161095 A1 | 6/2011 | Line et al. |
| 2011/0161163 A1 | 6/2011 | Carlson et al. |
| 2011/0161790 A1 | 6/2011 | Junior et al. |
| 2011/0191142 A1 | 8/2011 | Huang et al. |
| 2011/0208515 A1 | 8/2011 | Neuhauser |
| 2011/0213670 A1 | 9/2011 | Strutton et al. |
| 2011/0223571 A1 | 9/2011 | Farahat et al. |
| 2011/0224569 A1 | 9/2011 | Isenhart et al. |
| 2011/0225021 A1 | 9/2011 | Kantak et al. |
| 2011/0225043 A1 | 9/2011 | Bhatia et al. |
| 2011/0225049 A1 | 9/2011 | Bhatia et al. |
| 2011/0231240 A1 | 9/2011 | Schoen et al. |
| 2011/0237923 A1 | 9/2011 | Picht et al. |
| 2011/0237971 A1 | 9/2011 | Pradeep et al. |
| 2011/0246574 A1 | 10/2011 | Lento et al. |
| 2011/0248729 A2 | 10/2011 | Mueller et al. |
| 2011/0256520 A1 | 10/2011 | Siefert |
| 2011/0257502 A1 | 10/2011 | Lee |
| 2011/0257937 A1 | 10/2011 | Lee |
| 2011/0270620 A1 | 11/2011 | Pradeep et al. |
| 2011/0271312 A1* | 11/2011 | Arnouse ................ G06F 15/02 725/106 |
| 2011/0276504 A1 | 11/2011 | Pradeep et al. |
| 2011/0282231 A1 | 11/2011 | Pradeep et al. |
| 2011/0282232 A1 | 11/2011 | Pradeep et al. |
| 2011/0282749 A1 | 11/2011 | Pradeep et al. |
| 2011/0282880 A1 | 11/2011 | Krichman et al. |
| 2011/0296004 A1 | 12/2011 | Swahar |
| 2011/0298706 A1 | 12/2011 | Mann |
| 2011/0301431 A1 | 12/2011 | Greicius et al. |
| 2011/0313849 A1 | 12/2011 | Brueck et al. |
| 2011/0319975 A1 | 12/2011 | Ho et al. |
| 2012/0002848 A1 | 1/2012 | Hill |
| 2012/0004899 A1 | 1/2012 | Arshi |
| 2012/0022391 A1 | 1/2012 | Leuthardt |
| 2012/0035428 A1 | 2/2012 | Roberts et al. |
| 2012/0036004 A1 | 2/2012 | Pradeep et al. |
| 2012/0036005 A1 | 2/2012 | Pradeep et al. |
| 2012/0046993 A1 | 2/2012 | Hill |
| 2012/0054018 A1 | 3/2012 | Pradeep et al. |
| 2012/0072289 A1 | 3/2012 | Pradeep et al. |
| 2012/0072845 A1 | 3/2012 | John et al. |
| 2012/0072936 A1 | 3/2012 | Small et al. |
| 2012/0078065 A1 | 3/2012 | De Lemos et al. |
| 2012/0083668 A1 | 4/2012 | Pradeep et al. |
| 2012/0084139 A1 | 4/2012 | Pradeep et al. |
| 2012/0089552 A1 | 4/2012 | Chang et al. |
| 2012/0096363 A1 | 4/2012 | Barnes et al. |
| 2012/0108995 A1 | 5/2012 | Pradeep et al. |
| 2012/0114305 A1 | 5/2012 | Holden |
| 2012/0130800 A1 | 5/2012 | Pradeep et al. |

(56) References Cited

U.S. PATENT DOCUMENTS

| | | |
|---|---|---|
| 2012/0166252 A1 | 6/2012 | Walker |
| 2012/0173701 A1 | 7/2012 | Tenbrock |
| 2012/0203363 A1 | 8/2012 | McKenna et al. |
| 2012/0203559 A1 | 8/2012 | McKenna et al. |
| 2012/0239407 A1 | 9/2012 | Lynch et al. |
| 2012/0245978 A1 | 9/2012 | Jain et al. |
| 2012/0249797 A1 | 10/2012 | Haddick et al. |
| 2012/0254909 A1 | 10/2012 | Serdiuk |
| 2012/0272256 A1 | 10/2012 | Bedi |
| 2012/0284332 A1 | 11/2012 | Pradeep et al. |
| 2012/0290409 A1 | 11/2012 | Pradeep et al. |
| 2012/0290637 A1 | 11/2012 | Perantatos et al. |
| 2012/0296699 A1 | 11/2012 | Richardson et al. |
| 2012/0317198 A1 | 12/2012 | Patton et al. |
| 2013/0018949 A1 | 1/2013 | Pradeep |
| 2013/0022948 A1 | 1/2013 | Angell et al. |
| 2013/0024272 A1 | 1/2013 | Pradeep et al. |
| 2013/0046577 A1 | 2/2013 | Marci et al. |
| 2013/0060125 A1 | 3/2013 | Zeman et al. |
| 2013/0094722 A1 | 4/2013 | Hill |
| 2013/0097715 A1 | 4/2013 | Fourman |
| 2013/0121591 A1 | 5/2013 | Hill |
| 2013/0124365 A1 | 5/2013 | Pradeep |
| 2013/0143185 A1 | 6/2013 | Liu et al. |
| 2013/0145385 A1* | 6/2013 | Aghajanyan ........... G06Q 30/02 725/10 |
| 2013/0152506 A1 | 6/2013 | Pradeep |
| 2013/0166373 A1 | 6/2013 | Pradeep et al. |
| 2013/0183646 A1 | 7/2013 | Lusted et al. |
| 2013/0185140 A1 | 7/2013 | Pradeep et al. |
| 2013/0185141 A1 | 7/2013 | Pradeep et al. |
| 2013/0185142 A1 | 7/2013 | Pradeep et al. |
| 2013/0185144 A1 | 7/2013 | Pradeep et al. |
| 2013/0185145 A1 | 7/2013 | Pradeep et al. |
| 2013/0205314 A1* | 8/2013 | Ramaswamy ... H04N 21/44213 725/14 |
| 2013/0268279 A1 | 10/2013 | Srinivasan et al. |
| 2013/0280682 A1 | 10/2013 | Levine et al. |
| 2013/0304540 A1 | 11/2013 | Pradeep et al. |
| 2013/0311132 A1 | 11/2013 | Tobita |
| 2013/0332259 A1 | 12/2013 | Pradeep et al. |
| 2014/0025620 A1 | 1/2014 | Greenzeiger et al. |
| 2014/0058828 A1 | 2/2014 | el Kaliouby et al. |
| 2014/0067466 A1 | 3/2014 | Xiao et al. |
| 2014/0150002 A1* | 5/2014 | Hough ................ H04N 21/4415 725/9 |
| 2014/0162225 A1 | 6/2014 | Hill |
| 2014/0200416 A1 | 7/2014 | Kashef et al. |
| 2014/0214335 A1 | 7/2014 | Siefert |
| 2014/0221866 A1 | 8/2014 | Quy |
| 2014/0244345 A1 | 8/2014 | Sollis et al. |
| 2014/0278914 A1 | 9/2014 | Gurumoorthy et al. |
| 2014/0282646 A1* | 9/2014 | McCoy .............. G06K 9/00597 725/12 |
| 2014/0350431 A1 | 11/2014 | Hagedorn |
| 2015/0186923 A1 | 7/2015 | Gurumoorthy et al. |
| 2015/0213019 A1 | 7/2015 | Marvit et al. |
| 2016/0239139 A1* | 8/2016 | Wang .................... G06F 3/0416 |

FOREIGN PATENT DOCUMENTS

| | | |
|---|---|---|
| EP | 1808102 | 7/2007 |
| GB | 1374658 | 11/1974 |
| GB | 2221759 | 2/1990 |
| JP | 2001-147944 | 5/2001 |
| JP | 2005-51654 | 2/2005 |
| JP | 2005-160805 | 6/2005 |
| JP | 2006-227994 | 8/2006 |
| JP | 2006-305334 | 11/2006 |
| JP | 2006-6355 | 7/2007 |
| KR | 2004-22399 | 7/2006 |
| WO | 95-018565 | 7/1995 |
| WO | 1997-017774 | 5/1997 |
| WO | 1997-040745 | 11/1997 |
| WO | 1997-041673 | 11/1997 |
| WO | 02-100241 | 12/2002 |
| WO | 02-102238 | 12/2002 |
| WO | 2004-049225 | 6/2004 |
| WO | 2008030831 | 3/2008 |
| WO | 2008-055078 | 5/2008 |
| WO | 2008-064431 | 6/2008 |
| WO | 2008-077178 | 7/2008 |
| WO | 2008-109694 | 9/2008 |
| WO | 2008-109699 | 9/2008 |
| WO | 2008-121651 | 10/2008 |
| WO | 2008-137579 | 11/2008 |
| WO | 2008-137581 | 11/2008 |
| WO | 2008-141340 | 11/2008 |
| WO | 2008-154410 | 12/2008 |
| WO | 2009-018374 | 2/2009 |
| WO | 2009-052833 | 4/2009 |
| WO | 2011-055291 | 5/2011 |
| WO | 2011-056679 | 5/2011 |

OTHER PUBLICATIONS

Ambler, "Salience and Choice: Neural Correlates of Shopping Decisions," Psychology & Marketing, vol. 21, No. 4, p. 247-261, Wiley Periodicals, Inc., doi: 10.1002/mar20004, (Apr. 2004), 16 pages.

Bagozzi et al., "The Role of Emotions in Marketing," Journal of the Academy of Marketing Science, vol. 27, No. 2, pp. 184-206, Academy of Marketing Science (1999), 23 pages.

Belch et al., "Psychophysiological and Cognitive Response to Sex in Advertising," Advances in Consumer Research, vol. 9, pp. 424-427, (1982), 6 pages.

Blakeslee, "If You Have a 'Buy Button' in Your Brain, What Pushes It?" The New York Times, www.nytimes.com, (Oct. 19, 2004), 3 pages.

Braeutigam, "Neuroeconomics-From neural systems to economic behaviour," Brain Research Bulletin, vol. 67, pp. 355-360, Elsevier, (2005), 6 pages.

Buschman, et al., "Top-Down versus Bottom-Up Control of Attention in the Prefrontal and Posterior Parietal Cortices," Science, vol. 315, www.sciencemag.org/cgi/content/full/315/5820/1860, American Association for the Advancement of Science, (2007), 4 pages.

Canolty, et al., "High Gamma Power Is Phase-Locked to Theta Oscillations in Human Neocortex," Science, vol. 313, www.sciencemag.org, (Sep. 15, 2006), 3 pages.

Canolty, et al., "The functional role of cross-frequency coupling," Trends in Cognitive Sciences, Elsevier, (Nov. 2010) 11 pages.

Crawford et al., "Self-generated happy and sad emotions in low and highly hypnotizable persons during waking and hypnosis: laterality and regional EEG activity differences," International Journal of Psychophysiology, vol. 24, pp. 239-266, (Dec. 1996), 28 pages.

D'Esposito, "From cognitive to neural models of working memory," Philosophical Transitions of the Royal Society B, doi: 10.1098/rstb.2007.2086, (Mar. 30, 2007), 12 pages.

Davidson, et al., "The functional neuroanatomy of emotion and affective style," TRENDS in Cognitive Sciences, vol. 3, No. 1, (Jan. 1999), 11 pages.

Desmet, "Measuring Emotions: Development and Application of an Instrument to Measure Emotional Responses to Products," to be published in Funology: From Usability to Enjoyment, pp. 111-123, Kluwer Academic Publishers, (Blythe et al., eds., 2004), 13 pages.

EEG Protocols, "Protocols for EEG Recording," retrieved from the Internet on Aug. 23, 2011, http://www.q-metrx.com/EEGrecordingProtocols.pdf, (Nov. 13, 2007), 3 pages.

Fogelson, et al., "Prefrontal cortex is critical for contextual processing: evidence from brain lesions," Brain: A Journal of Neurology, vol. 132, pp. 3002-3010, doi:10.1093/brain/awp230, (Aug. 27, 2009), 9 pages.

Fries, Pascal, "A mechanism for cognitive dynamics: neuronal communication through neuronal coherence," Trends in Cognitive Sciences, vol. 9, No. 10, pp. 474-480, Elsevier B.V. www.sciencedirect.com, (Oct. 2005), 7 pages.

(56) References Cited

OTHER PUBLICATIONS

Fuster, Joaquin M., "Cortex and Memory: Emergence of a New Paradigm," Journal of Cognitive Neuroscience, vol. 21, No. 11, pp. 2047-2072, Massachusetts Institute of Technology, (Nov. 2009), 26 pages.
Gazzaley et al., "Top-down Enhancement and Suppression of Magnitude and Speed of Neural Activity," Journal of Cognitive Neuroscience, vol. 17, No. 3, pp. 507-517, Massachusetts Institute of Technology, (2005), 11 pages.
Haq, Amber, "This Is Your Brain on Advertising," BusinessWeek, Market Research, (Oct. 8, 2007), 4 pages.
Hartikainen et al., Manuscript Draft of "Emotionally arousing stimuli compete with attention to left hemispace," NeuroReport, (Sep. 8, 2007), 26 pages.
Hazlett et al., "Emotional Response to Television Commercials: Facial EMG vs. Self-Report," Journal of Advertising Research, (Apr. 1999), 17 pages.
Boltz, M.G., "The cognitive processing of film and musical soundtracks", Memory & Cognition, 32(7):1194-1205 (2004), 12 pages.
Christie et al., "Autonomic specificity of discrete emotion and dimensions of affective space: a multivariate approach", Int'l J. Psychophysiol., 51:143-153 (2004), 11 pages.
Coombes et al., "Emotion and movement: Activation of defensive circuitry alters the magnitude of a sustained muscle contraction", Neurosci. Lett., 396:192-196 (2006), 5 pages.
Cryer et al., "Pull the plug on stress", Harv. Bus. Rev., 81(7):102-107 (2003), 8 pages.
Demaree et al., "Predicting facial valence to negative stimuli from resting RSA: Not a function of active emotion regulation", Cognition and Emotion, 20(2):161-176 (2006), 6 pages. (Abstract provided).
Ekman et al., "Autonomic Nervous System Activity Distinguishes among Emotions", Science, 221(4616):1208-1210 (1983), 5 pages.
Elton, C., "Measuring emotion at the symphony", http://www.boston.com, pp. 1-3 (2006), 3 pages.
Goldberg, C., "Getting wired could help predict emotions", http://www.boston.com, pp. 1-4 (2005), 4 pages.
Gomez et al., "Respiratory responses associated with affective processing of film stimuli", Biol. Psychol., 68:223-235 (2005), 2 pages. (Abstract provided).
Hall, B.F., "Advertising as a Factor of production", Admap, pp. 30-32 (2003), 1 page. (Abstract provided).
Hall, B.F., "Is cognitive processing the right dimension", Admap, pp. 37-39 (2003), 3 pages.
Hall, B.F., "On Measuring the Power Communications", JAR, pp. 1-11 (2004), 1 page. (Abstract provided).
Hall, B.F., "Research and strategy: a fall from grace", Admap, pp. 2-4 (2003), 1 page. (Abstract provided).
Hubert, et al., "Autonomic, neuroendocrine, and subjective responses to emotion-inducing film stimuli", Int'l J. Psychophysiol., 11:131-140 (1991), 2 pages. (Abstract provided).
Levenson et al., "Emotion and Autonomic Nervous System Activity in the Minangkabau of West Sumatra", J. Personality Soc. Psychol., 62(6):972-988 (1992), 2 pages. (Abstract provided).
Marci et al., "The Effect of Emotional Distance on Pyschophysiologic Concordance and Perceived Empathy Between Patient and Interviewer", Appl. Psychophysiol. Biofeedback, 31:115-129 (2006), 8 pages. (Abstract provided).
McCraty et al., "Analysis of twenty-four hour heart rate variability in patients with panic disorder", Biol. Psychol., 56(2):131-150 (2001), 1 page. (Abstract provided).
McCraty et al., "Electrophysiolocial Evidence of Intuition: Part 1. The Surprising Role of the Heart", J. Altern. Complement. Med., 10(1):133-143 (2004), 12 pages.
McCraty et al., "Electrophysiological Evidence of Intuition: Part 2. A System-Wide Process?", J. Altern. Complement. Med., 10(2\0):325-336 (2004), 12 pages.
McCraty et al., "Impact of a Workplace Stress Reduction Program on Blood Pressure and Emotional Health in Hypertensive Employees", J. Altern. Complement. Med., 9(3):355-369 (2003), 15 pages.
McCraty et al., "The Effects of Different Types of Music on Mood, Tension, and Mental Clarity", Altern. Ther. Health Med., 4(1):75-84 (1998), 10 pages.
McCraty et al., "The Effects of Emotions on Short-Term Power Spectrum Analysis of Heart Rate Variability", Am. J Cardiol., 76(14):1089-1093 (1995), 6 pages.
McCraty et al., "The Impact of a New Emotional Self-Management Program on Stress, Emotions, Heart Rate Variability, DHEA and Cortisol", Intergr. Physiol. Behav. Sci., 33(2):151-170 (1998), 20 pages.
McCraty et al., "The Impact of an Emotional Self-Management Skills Course on Psychosocial Functioning and Autonomic Recovery to Stress in Middle School Children", Integr. Physiol. Behav. Sci., 34(4):246-268 (1999), 23 pages.
Melillo, W., "Inside the consumer mind: What Neuroscience can tell us about marketing", http://www.answerstream.com, pp. 1-13 (2006), 8 pages.
Miller et al., "Influence of Specific Emotional States on Autonomic Reactivity and Pulmonary Function in Asthmatic Children", J. Am. Acad. Child Adolescent Psychiatry, 36(5):669-677 (1997), 3 pages. (Abstract provided).
Murphy et al., "The Heart Reinnervates After Transplantation", Ann. Thorac. Surg., 69(6):1769-1781 (2000), 13 pages.
Ranii, D., "Adding Science to Gut Check", The News & Observer, pp. 1 (2005).
Rosenberg, K., "Emotional R.O.I.", The Hub, pp. 24-25 (2006), 2 pages.
Tiller et al., "Cardiac Coherence: A New, Noninvasive Measure of Autonomic Nervous System Order", Altern. Ther. Health Med., 2(1):52-65 (1996), 14 pages.
Umetani et al., "Twenty-Four Hour Time Domain Heart Rate Variability and Heart Rate: Relations to Age and Gender Over Nine Decades", J. Am. Coll. Cardiol., 31(3):593-601 (1998), 9 pages.
Von Leupoldt et al., "Emotions in a Body Plethysmograph", J. Psychophysiol., 18(4):170-176 (2004), 1 page. (Abstract provided).
Kallman, H. Effect of Blank Time on Picture Recognition. The American Journal of Psychology, vol. 97, No. 3, Autumn, 1984, pp. 399-406 [retrieved on Nov. 3, 2011]. Retrieved from the Internet: <URL: http://www.jstor.org/pss/1422527>,4 pages. (Abstract provided).
Larose, Daniel T., Data Mining Methods and Models, John Wiley & Sons, Inc., 2006.
Han, Micheline Kamber Jiawei, Data Mining: Concepts and Techniques, Second Edition (The Morgan Kaufmann Series in Data Management Systems), Elsevier, Inc., 2006.
Liu, Bing, Web Data Mining: Exploring Hyperlinks, Contents, and Usage Data (Data-Centric Systems and Applications), Springer-Verlag, 2007.
Berry, Michael J.A. and Linoff, Gordon S., Data Mining Techniques: For Marketing, Sales, and Customer Relationship Management, John Wiley & Sons, Inc., 1997.
Watching ADS Is Real Science Research Companies Monitor Physiological Reactions to Commercials to Determine Their Effectiveness.: [3 Star Edition] Bruce Horovitz Los Angeles Times. Orlando Sentinel [Orlando, Fla] Sep. 1, 1991; D1, 2pgs.
Wearable feedback systems for rehabilitation Sung, Michael; Marci, Carl; Pentland, Alex. Journal of NeuroEngineering and Rehabilitation 2 (2005), 2pgs.
Keren et al., "Saccadic spike potentials in gamma-band EEG: Characterization, detection and suppression," NeuroImage, http://dx.doi:10.1016/j.neuroimage.2009.10.057, (Oct. 2009), 16 pages.
Kishiyama et al., "Novelty Enhancements in Memory Are Dependent on Lateral Prefrontal Cortex," The Journal of Neuroscience, pp. 8114-8118, Society for Neuroscience (Jun. 24, 2009), 5 pages.
Knight, Robert T., "Contribution of human hippocampal region to novelty detection," Nature, vol. 383, www.nature.com, (Sep. 19, 1996), 4 pages.

(56) References Cited

OTHER PUBLICATIONS

Knight, Robert T., "Decreased Response to Novel Stimuli after Prefrontal Lesions in Man," Electroencephalography and Clinical Neurophysiology, vol. 59, pp. 9-20, Elsevier Scientific Publishers Ireland, Ltd., (1984), 12 pages.
Lee et al., "What is 'neuromarketing'? A discussion and agenda for future research," International Journal of Psychophysiology, vol. 63, pp. 199-204, Elsevier (2006), 6 pages.
Lekakos, George, "Personalized Advertising Services Through Hybrid Recommendation Methods: The Case of Digital Interactive Television," Department of Informatics, Cyprus University, (2004), 11 pages.
Lewis et al., "Market Researchers make Increasing use of Brain Imaging," ACNR, vol. 5, No. 3, pp. 36-37, (Jul./Aug. 2005), 2 pages.
Lui et al., "Marketing Strategies in Virtual Worlds," The Data Base for Advances in Information Systems, vol. 38, No. 4, pp. 77-80, (Nov. 2007), 4 pages.
Makeig et al., "Dynamic Brain Sources of Visual Evoked Responses," Science, vol. 295, www.sciencemag.org, (Jan. 25, 2002), 5 pages.
Makeig et al., "Mining event-related brain dynamics," TRENDS in Cognitive Sciences, vol. 8, No. 5, (May 2004), www.sciencedirect.com, 7 pages.
Miltner et al., "Coherence of gamma-band EEG activity as a basis for associative learning," Nature, vol. 397, www.nature.com, (Feb. 4, 1999), 3 pages.
Moran et al. "Peak frequency in the theta and alpha bands correlates with human working memory capacity," frontiers in Human Neuroscience, vol. 4, Article 200, www.frontiersin.org, (Nov. 11. 2010), 12 pages.
Neurofocus—Neuroscientific Analysis for Audience Engagement, accessed on Jan. 8, 2010 at http://web.archive.org/web/20080621114525/www.neurofocus.com /BrandImage.htm, (2008), 2 pages.
Nielsen, "Neuroinformatics in Functional Neuroimaging," Informatics and Mathematical Modeling, Technical University of Denmark, (Aug. 30, 2002), 241 pages.
Page et al., "Cognitive Neuroscience, Marketing and Research," Congress 2006—Foresight—The Predictive Power of Research Conference Papers, ESOMAR Publications, (Sep. 17, 2006), 25 pages.
Simon-Thomas et al, "Behavioral and Electrophysiological Evidence of a Right Hemisphere Bias for the Influence of Negative Emotion on Higher Cognition," Journal of Cognitive Neuroscience, pp. 518-529, Massachusetts Institute of Technology (2005), 12 pages.
Sutherland, Max, "Neuromarketing: What's it all about?" Retrieved from Max Sutherland's Weblog on Aug. 23, 2011, http://www.sutherlandsurvey.com/Column_pages/Neuromarketing_whats_it_all_about.htm, (Mar. 2007), 5 pages.
Swick et al., "Contributions of Prefrontal Cortex to Recognition Memory: Electrophysiological and Behavioral Evidence," Neuropsychology, vol. 13, No. 2, pp. 155-170, American Psychological Association, Inc. (1999), 16 pages.
Voytek et al., "Shifts in gamma phase-amplitude coupling frequency from theta to alpha over posterior cortex during visual tasks,"Frontiers in Human Neuroscience, doi: 10.3389/fnhum.2010.00191, (Oct. 19, 2010), 9 pages.
Wang, Xiao-Jing, "Neurophysiological and Computational Principles of Cortical Rhythms in Cognition," Physiol Rev 90: pp. 1195-1268, American Physiological Society, www.prv.org, (2010), 75 pages.
Woodman et al., "Serial Deployment of Attention During Visual Search.," Journal of Experimental Psychology: Human Perception and Performance, vol. 29, No. 1, pp. 121-138, American Physiological Association (2003), 18 pages.
Yuval-Greenberg et al., "Transient Induced Gamma-Bands Response in EEG as a Manifestation of Miniature Saccades," Neuron, vol. 58, pp. 429-441, Elsevier Inc. (May 8, 2008), 13 pages.
Ziegenfuss, Jennifer S., "Neuromarketing: Advertising Ethical & Medical Technology," The Brownstone Journal, vol. XII, Boston University, pp. 69-73, (May 2005), 9 pages.
Zyga, Lisa, "A Baseball Cap That Can Read Your Mind," PhysOrg.com, located at www.physorg.com/news130152277.html, (May 16, 2008), 11 pages.
Ambler et al., "Ads on the Brain; A Neuro-Imaging Comparison of Cognitive and Affective Advertising Stimuli," London Business School, Centre for Marketing Working Paper, No. 00-902, (Mar. 2000), 23 pages.
Clifford, Stephanie, "Billboards That Look Back," The New York Times, NYTimes.com, available at http://www.nytimes.com/2008/05/31/business/media/31billboard.html, (May 31, 2008), 4 pages.
Bimler et al., "Categorical perception of facial expressions of emotion: Evidence from multidimensional scaling," Cognition and Emotion, vol. 15(5), pp. 633-658 (Sep. 2001), 26 pages.
de Gelder et al., "Categorical Perception of Facial Expressions: Categories and their Internal Structure," Cognition and Emotion, vol. 11(1), pp. 1-23 (1997), 23 pages.
Newell et al., "Categorical perception of familiar objects," Cognition, vol. 85, Issue 2, pp. 113-143 (Sep. 2002), 31 pages.
Padgett et al., "Categorical Perception in Facial Emotion Classification," In Proceedings of the 18th Annual Conference of the Cognitive Science Society, pp. 249-253 (1996), 5 pages.
Klimesch, Wolfgang, "EEG alpha and theta oscillations reflect cognitive and memory performance a review and analysis," Brain Research Reviews, vol. 29, 169-195, (1999), 27 pages.
Krakow et al., "Methodology: EEG-correlated fMRI," Functional Imaging in the Epilepsies, (Lippincott Williams & Wilkins, 2000), 17 pages.
Krugman, "Brain Wave Measures of Media Involvement," Journal of Advertising Research vol. 11, No. 1, pp. 3-9 (Feb. 1971), 7 pages.
Palva et al., "Phase Synchrony Among Neuronal Oscillations in the Human Cortex," Journal of Neuroscience 25 (2005), 3962-3972, 11 pages.
Lachaux et al., "Measuring Phase Synchrony in Brain Signals," Human Brain Mapping 8 (1999), 194-208, 15 pages.
Zhang, P., "Will You Use Animation on Your Web Pages?" Doing Business on the Internet: Opportunities and Pitfalls, C. Romm and F. Sudweeks (eds.), Spring-Verlag (1999), 17 pages.
Coan et al., "Voluntary Facial Expression and Hemispheric Asymmetry Over the Frontal Cortex," Psycophysiology (Nov. 2001), 912-924, 14 pages.
Duchowski, "A Breadth-First Survey of Eye-tracking Applications," Beahavior Research Methods, Instruments, and Computers (Nov. 2002), 455-470, 16 pages.
Heo et al., "Wait! Why is it Not Moving? Attractive and Distractive Ocular Responses to Web Ads," Paper presented to AEJMC, (Aug. 2001) Washington, DC, available at http://www.psu.edu/dept/medialab/researchpage/newabstracts/wait.html, 3 pages.
Rothschild et al., "Predicting Memory for Components of TV Commercials from EEG," Journal of Consumer Research (Mar. 1990), p. 472-478, 8 pages.
Beaver, John D., et al., "Individual Differences in Reward Drive Predict Neural Responses to Images of Food", J. of Neuroscience, (May 10, 2006), 5160-5166, 7 pages.
Shandlen et al., "A Computational Analysis of the Relationship between Neuronal and Behavioral Responses to Visual Motion", The Journal of Neuroscience, (Feb. 15, 1996) 1486-1510, 25 pages.
Cassanello et al., "Neuronal Responses to Moving Targets in Monkey Frontal Eye Fields", J Neurophysiol (Sep. 2008), 1544-1556, 16 pages.
Bandari et al., "The Pulse of News in Social Media: Forecasting Popularity," ICWSM, Feb. 2012, 9 pages.
Rodriguez et al., "Social Networks for News Media Distribution," STB-RL: Digital Library Research and Prototyping, Los Alamos National Laboratory, 2006, 6 pages.
Brown, M. "Should My Advertising Stimulate an Emotional Response?" 2009, available at http://www.wpp.com/~/media/sharedwpp/readingroom/marketing/millward_brown_emotional_response.pdf, 6 pages.

(56) References Cited

OTHER PUBLICATIONS

Mehta, A. et al., "Reconsidering Recall and Emotion in Advertising," Journal of Advertising Research, Mar. 2006, pp. 49-56, 8 pages.
Micu, A. C. et al., "Measurable Emotions: How Televistion Ads Really Work: How to Patterns of Reactions to Commercials can Demonstrate Advertising Effectiveness", Management Slant, 50(2), Jun. 2010; pp. 1-17, 18 pages.
Cheung, Kwok-Wai, et al., "Mining Customer Product Ratings for Personalized Marketing," Decision Support Systems 35, 2003, pp. 231-243, 13 pages.
Jaimes, A., Sebe, N., Multimodal Human-Computer Interaction: A Survey, Computer Vision and Image Understanding 108, Oct.-Nov. 2007, pp. 116-134, 19 pages.
Garton, L. et al., "Studying Online Social Networks", Journal of Computer-Mediated Communication , 3(1), Jun. 1997, 29 pages.
Darrow, Chester, "Psychological and psychophysiological significance of the electroencephalogram," Psychological Review (May 1947) 157-168, 12 pages.
Stamm, John, "On the Relationship between Reaction Time to Light and Latency of Blocking the Alpha Rhythm," Electroencephalography and Clinical Neurophysiology (Feb. 1952), 61-68, 8 pages.
Mizuki, Yashushi, et al., "Periodic Appearance of the Theta Rhythm in the Frontal Midline Area During Performance of a Mental Task,:" Electroencephalography and Clinical Neurophysiology (Aug. 1980), 345-351, 7 pages.
Ekman, P., Friesen, W., Measuring Facial Movement, Environmental Psychology and Nonverbal Behavior, 1 (1) (Fall 1976), pp. 56-75, 20 pages.
Ekman, P., Friesen, W., Ancoli, S., Facial Signs of Emotional Experience, J. Personality & Social Psychology, 39(6) (Dec. 1980), pp. 1125-1134, 10 pages.
Jia, X., Nixon, M.S., Extending the Feature Set for Automatic Face Recognition, International Conference on Image Processing and Its Applications (Apr. 7-9, 1992), 6 pages.
Lisetti, C., Nasoz, F., Using Noninvasive Wearable Computers to Recognize Human Emotions from Physiological Signals, EURASIP J. Applied Signal Processing, 11 (Sep. 2004), pp. 1672-1687, 16 pages.
McClure, Samuel, et al., "Neural Correlates of Behavioral Preference for Culturally Familiar Drinks," Neuron (Oct. 14, 2004), 379-387, 9 pages.
Opitz, S. "Neuromarketing: An Introduction" PowerPoint Presentation (2008), available at http://www.powershow.com/view/94a7b-Yz1mN/Neuromarketing_powerpoint_ppt_presentation (last accessed Oct. 14, 2015), 20 pages.
Axis Communications, "Improve your merchandising effectiveness. Get the full picture with network video" (2008), available at :http://www.axis.com/files/user_scenarios/ap_ret_merchandising_311 07_en_0803_1o.pdf, 2 pages.
Kamba, Tomonari, "The Krakatoa Chronicl—Interactive, Personalized Newspaper on the Web," available at: http://www.w3.org/Conferences/WWW4/Papers/93/ (last accessed Nov. 2, 2015), 15 pages.
Ehrenberg et al. , "Understanding Brand Performance Measures: Using Dirichlet Benchmarks," 2004, Journal of Business Research, vol. 57, pp. 1307-1325, 19 pages.
Leeflang et al. , "Building Models for Marketing Decisions," 2000, Springer Science + Business Media, pp. 192-235, 482-521, 86 pages.
Bassi et al., "The Dirichlet Model: Analysis of a Market and Comparison of Estimation Procedures," 2011, Marketing Bulletin, vol. 22, Technical Note 1, pp. 1-11, 11 pages.
Bhattacharya, "Is your brand's loyalty too much, too little, or just right?: Explaining deviations in loyalty from the Dirichlet norm," 1997, International Journal of Research in Marketing, vol. 14, pp. 421-435, 15 pages.
Cohen, "Differentiated product demand analysis with a structured covariance probit: A Bayesian econometric approach," 2009, PhD dissertation, University of Connecticut, pp. 1-184, 197 pages.
Nikolaeva et al., "The Moderating Role of Consumer and Product Characteristics on the Value of Customized On-Line Recommendations," 2006, International Journal of Electronic Commerce, vol. 11, No. 2, pp. 101-123, 24 pages.
Ehrenberg, "New Brands and the Existing Market," 1991, International Journal of Market Research, vol. 33, No. 4, 10 pages.
Foxall, "The Substitutability of Brands," 1999, Managerial and Decision Economics, vol. 20, pp. 241-257, 17 pages.
Pammer, "Forecasting the Penetration of a New Product—A Bayesian Approach," 2000, Journal of Business and Economic Statistics, vol. 18, No. 4, pp. 428-435, 8 pages.
Rungie et al., "Calculation of Theoretical Brand Performance Measures from the Parameters of the Dirichlet Model," 2004, Marketing Bulletin, Massey University, 15, Technical Note 2, pp. 1-19, 20 pages.
Uncles et al., "Patterns of Buyer Behavior: Regularities, Models, and Extensions," 1995, Marketing Science, vol. 14, No. 3, pp. G71-G78, 9 pages.
Becker, S. "A Study of Web Usability for Older Adults Seeking Online Health Resources," ACM Transactions on Computer-Human Interaction, vol. 11, No. 4, pp. 387-406 (Dec. 2004), 20 pages.
Knutson et al., "Neural Predictors of Purchases," Neuron vol. 53 (Jan. 4, 2007), pp. 147-156, 10 pages.
Schaefer et al., "Neural Correlates of Culturally Familiar Brands of Car Manufacturers," NeuroImage, vol. 31 (2006), pp. 861-865, 5 pages.
Aharon et al., "Beautiful Faces Have Variable Reward Value: fMRI and Behavorial Evidence," Neuron, vol. 32 (2001), pp. 537-551, 15 pages.
Landau et al., "Different Effects of Voluntary and Involunatry Attention on EEG Activity in the Gamma Band," J of Neuroscience 27(44), Oct. 31, 2007, pp. 11986-11990, 5 pages.
M. Corbetta et al., "Control of Goal-Directed and Stimulus-Driven Attention in the Brain," Nature Reviews Neuroscience, vol. 3, pp. 201-215, 15 pages, (Mar. 2002).
Hall, "Advertising as a Factor of Production," ADMAP, 2003, pp. 20-23, 1 page. (Abstract provided).
Tapert, Susan F., et al., "Neural Response to Alcohol Stimuli in Adolescents With Alcohol Use Disorder", Arch Gen Psychiatry (Jul. 2003), 727-735, 9 pages.
Barcelo, Francisco, et al., "Prefrontal Modulation of Visual Processing in Humans," Nature Neuroscience, vol. 3, No. 4, Apr. 2000, pp. 399-403.
Engel, Andreas, et al., "Dynamic Predictions: Oscillations and Synchrony in Top-Down Processing," Macmillan Magazines Ltd, vol. 2, Oct. 2001, pp. 704-716.
Merriam-Webster Online Dictionary, Definition for "Resonance," available at http://www.merriam-webster.com/dictionary/resonance, 4 pages.
Enghoff, Sigurd, Thesis: "Moving ICA and Time-Frequency Analysis in Event-Related EEG Studies of Selective Attention," Technical University of Denmark, (Dec. 1999), 54 pages.
Edgar, et al., "Digital Filters in ERP Research," in Event-Related Potentials: A Methods Handbook pp. 85-113, (Todd C. Handy, ed., 2005), 15 pages.
Flinker, A. et al, "Sub-centimeter language organization in the human temporal lobe," Brain and Language, Elsevier Inc., (2010), doi.org/10.1016/j.band1.2010.09.009, 7 pages.
Friedman, et al., "Event-Related Potential (ERP) Studies of Memory Encoding and Retrieval: A Selective Review," Microscopy Research and Technique 51:6-26, Wiley-Less, Inc. (2000), 23 pages.
Gaillard, "Problems and Paradigms in ERP Research," Biological Psychology, Elsevier Science Publisher B.V. (1988), 10 pages.
Hopf, et al., "Neural Sources of Focused Attention in Visual Search," Cerebral Cortex, 10:1233-1241, Oxford University Press, (Dec. 2000), 9 pages.
Luck, et al., "The sped of visual attention in schizophrenia: Electrophysiological and behavioral evidence," Schizophrenia Research, pp. 174-195, Elsevier B.V. www.sciencedirect.com, (2006), 22 pages.
Herrmann, et al., "Mechanisms of human attention: event-related potentials and oscillations," Neuroscience and Biobehavioral

(56) References Cited

OTHER PUBLICATIONS

Reviews, pp. 465-476, Elsevier Science Ltd., www.elsvevier.com/locate/neubiorev, (2001), 12 pages.

Knight, "Consciousness Unchained: Ethical Issues and the Vegetative and minimally Conscious State," The American Journal of Bioethics, 8:9, 1-2, http://dx.doi.org/10.1080/15265160802414524, (Sep. 1, 2008), 3 pages.

Paller, et al., "Validating neural correlates of familiarity," TRENDS in Cognitive Sciences, vol. 11, No. 6, www.sciencedirect.com, (May 2, 2007), 8 pages.

Picton, et al., "Guidelines for using human event-related potentials to study cognition: Recording standards and publication criteria," Psychophysiology, pp. 127-152, Society for Psychophysiological Research, (2000), 26 pages.

Yamaguchi, et al., "Rapid-Prefrontal—Hippocampal Habituation to Novel Events," The Journal of Neuroscience, pp. 5356-5363, Society for Neuroscience, (Apr. 29, 2004), 8 pages.

Rugg, et al., "Event-related potentials and recognition memory," TRENDS in Cognitive Sciences, vol. 11, No. 6, www.sciencedirect.com, (May 3, 2007), 7 pages.

Rugg, et al., "The ERP and cognitive psychology: conceptual issues," (Sep. 1996), 7 pages.

Kishiyama, et al., "Socioeconomic Disparities Affect Prefrontal Function in Children," Journal of Cognitive Neuroscience pp. 1106-1115, Massachusetts Institute of Technology, (2008), 10 pages.

Spencer, "Averaging, Detection, and Classification of Single-Trial ERPs," in Event-Related Potentials: A Methods Handbook, pp. 209-227, (Todd C. Handy, ed., 2005), 10 pages.

Srinivasan, "High-Resolution EEG: Theory and Practice," in Event-Related Potentials: A Methods Handbook, pp. 167-188, (Todd C. Handy, ed., 2005), 12 pages.

Taheri, et al., "A dry electrode for EEG recording," Electroencephalography and clinical Neurophysiology, pp. 376-383, Elsevier Science Ireland Ltd. (1994), 8 pages.

Talsma, et al., "Methods for the Estimation and Removal of Artifacts and Overlap in ERP Waveforms," in Event-Related Potentials: A Methods Handbook, pp. 115-148, (Todd C. Handy, ed., 2005), 22 pages.

Vogel, et al., "Electrophysiological Evidence for a Postperceptual Locus of Suppression During the Attentional Blink," Journal of Experimental Psychology: Human Perception and Performance, vol. 24, No. 6, pp. 1656-1674, (1998), 19 pages.

Rizzolatti et al., "The Mirror-Neuron System," Annu. Rev. Neurosci., vol. 27, pp. 169-192, (Mar. 5, 2004), 30 pages.

Voytek, et al., "Prefrontal cortex and basal ganglia contributions to visual working memory," PNAS Early Edition, www.pnas.org/cgi/doi/10.1073/pnas.1007277107, (2010), 6 pages.

Voytek, et al., "Hemicraniectomy: A New Model for Human Electrophysiology with High Spatio-temporal Resolution," Journal of Cognitive Neuroscience, vol. 22, No. 11, pp. 2491-2502, Massachusetts Institute of Technology, (Nov. 2009) 12 pages.

Woldorf, "Distortion of ERP averages due to overlap from temporally adjacent ERPs: Analysis and correction," Psychophysiology, Society for Psychophysiological Research, Cambridge University Press (1993), 22 pages.

Filler, "MR Neurography and Diffusion Tensor Imaging: Origins, History & Clinical Impact of the first 50,000 Cases With an Assortment of Efficacy and Utility in a Prospective 5,000 Patent Study Group," Institute for Nerve Medicine, (Nov. 7, 2008), 56 pages.

Knight, et al., "Prefrontal cortex regulates inhibition and excitation in distributed neural networks," Acta Psychologica vol. 101, pp. 159-178, Elsevier (1999), 20 pages.

Akam, et al., "Oscillations and Filtering Networks Support Flexible Routing of Information," Neuron, vol. 67, pp. 308-320, Elsevier, (Jul. 29, 2010), 13 pages.

Gargiulo et al., "A Mobile EEG System With Dry Electrodes," (Nov. 2008), 4 pages.

Badre, et al. "Frontal Cortex and the Discovery of Abstract Action Rules," Neuron, vol. 66, pp. 315-326, Elsevier, (Apr. 29, 2010), 13 pages.

Buschman, et al., "Serial, Covert Shifts of Attention during Visual Search Are Reflected by the Frontal Eye Fields and Correlated with Population Oscillations," Neuron, vol. 63, pp. 386-396, Elsevier, (Aug. 13, 2009), 11 pages.

Cheng, et al. "Gender Differences I the Mu Rhythm of the Human Mirror-Neuron System," PLos ONE, vol. 3, Issue 5, www.plosone.org, (May 2008), 7 pages.

Dien, et al., "Application of Repeated Measures ANOVA to High-Dens Dataset: A Review and Tutorial," in Event-Related Potentials: A Methods Handbook pp. 57- 82, (Todd C. Handy, ed., 2005), 14 pages.

William, "Brain Signals to Control Movement of Computer Cursor," Blog article: Brain Signals to Control Movement of Computer Cursor, Artificial Intelligence, retrieved from the Internet on Aug. 17, 2011, http://whatisartificialintelligence.com/899/brain-signals-to-control-movement-of-computer-cursod, (Feb. 17, 2010), 3 pages.

Ruchkin et al., "Modality-specific processing streams in verbal working memory: evidence from spatio-temporal patterns of brain activity," Cognitive Brain Research, vol. 6, pp. 95-113, Elsevier, (1997), 19 pages.

Kay et al., "Identifying natural images from human brain activity," Nature, vol. 452, pp. 352-356, Nature Publishing Group, (Mar. 20, 2008), 5 pages.

Anonymous, "Functional magnetic resonance imaging," retrieved online from Wikipedia, the Free Encyclopedia on Aug. 23, 2011, at http://en.wikipedia.org/w/index.php?title=Functional_magnetic_resonance_imaging&oldid=319601772, (Oct. 13, 2009), 8 pages.

Osborne, "Embedded Watermarking for image Verification in Telemedicine," Thesis submitted for the degree of Doctor of Philosophy, Electrical and Electronic Engineering, University of Adelaide (2005), 219 pages.

Arousal in Sport, in Encyclopedia of Applied Psychology, vol. 1, p. 159, retrieved from Google Books, (Spielberger, ed., Elsevier Academic Press, 2004), 1 page.

Yap et al., "TIMER: Tensor Image Morphing for Elastic Registration," NeuroImage, vol. 47, (May 3, 2009), 15 pages.

Clemons, "Resonance Marketing in the Age of the Truly Informed Consumer: Creating Profits through Differentiation and Delight," Wharton Information Strategy & Economics Blog 2, available at http://opim.wharton.upenn.edu/~clemons/blogs/resonanceblog.pdf, (Mar. 28, 2007), 8 pages.

Meriam Webster Online Dictionary, Definition of Virtual Reality, available at http://www.meriam-webster.com/dictionary/virtual%20reality, 2 page.

Griss et al., "Characterization of micromachined spiked biopotential electrodes," Biomedical Engineering, IEEE Transactions (Jun. 2002), 8 pages.

"User monitoring," Sapien Systems, available at http://web.archive.org/web/20030818043339/http:/www.sapiensystems.com/eyetracking.html, (Aug. 18, 2003), 1 page.

Sullivan et al., "A brain-machine interface using dry-contact, low-noise EEG sensors," In Proceedings of the 2008 IEEE International Symposium on Circuits and Systems, (May 18, 2008), 4 pages.

Barreto et al., "Physiologic Instrumentation for Real-time Monitoring of Affective State of Computer Users," WSEAS International Conference on Instrumentation, Measurement, Control, Circuits and Systems (IMCCAS), (2004), 6 pages.

Jung et al., "Analysis and Visualization of Single-Trial Event-Related Potentials," Human Brain Mapping vol. 14, 166-185 (2001), 20 pages.

The Mathworks, Inc., "MATLAB Data Analysis: Version 7," p. 4-19 (2005), 3 pages.

Allen et al., "A Method of Removing Imaging Artifact from Continuous EEG Recorded during Functional MRI," NeuroImage, vol. 12, 230-239, (Aug. 2000).

Oberman et al., "EEG evidence for mirror neuron activity during the observation of human and robot actions: Toward an analysis of the human qualities of interactive robots," Elsevier, Neurocomputing vol. 70 (2007), Jan. 2, 2007 (10 pages).

(56) References Cited

OTHER PUBLICATIONS

Meriam-Webster Online Dictionary definition for "tangible," available at http://www.meriam-webster.com/dictionary/tangible, 1 page.
Mosby's Dictionary of Medicine, Nursing, & Health Professions, 2009, Mosby, Inc., Definition of Alpha Wave, 1 page.
Mosby's Dictionary of Medicine, Nursing, & Health Professions, 2009, Mosby, Inc., Definition of Beta Wave, 1 page.

* cited by examiner

METHODS AND APPARATUS TO ADJUST CONTENT PRESENTED TO AN INDIVIDUAL

RELATED APPLICATIONS

This patent claims priority to U.S. Provisional Application Ser. No. 62/163,874, which was filed on May 19, 2015 and U.S. Provisional Application Ser. No. 62/272,423, which was filed on Dec. 29, 2015 and are hereby incorporated herein by reference in their entireties.

FIELD OF THE DISCLOSURE

This disclosure relates generally to presenting content to an individual and, more particularly, to methods and apparatus to adjust content presented to an individual.

BACKGROUND

Individuals are exposed to multiple passive and interactive audio, visual, and audio-visual media content every day. The media content produces biologically based responses in the user that can be measured by one or more sensors. An individual's biological and/or physical response to an image can indicate emotional and cognitive responses. Personal logs and self-reporting of responses are often inaccurate and include biases due to human input. Additionally, personal logs and self-reporting rely on an accurate account by the individual of their own emotional and cognitive reaction.

BRIEF DESCRIPTION OF THE DRAWINGS

The figures are not to scale. Wherever possible, the same reference numbers will be used throughout the drawing(s) and accompanying written description to refer to the same or like parts.

DETAILED DESCRIPTION

Figure 1:
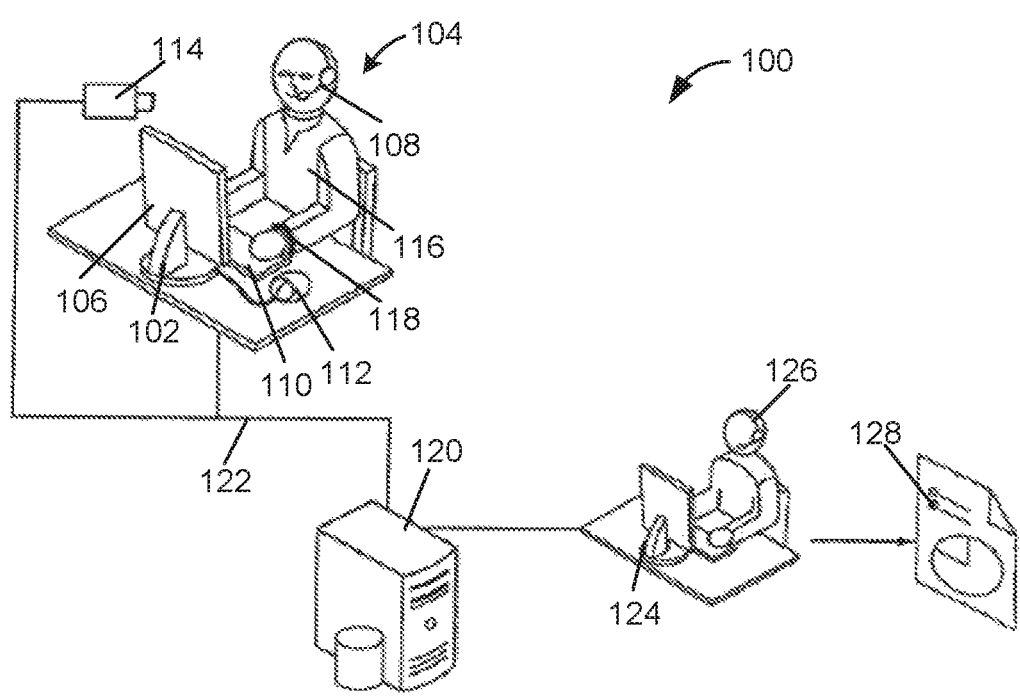
FIG. 1 is a schematic illustration of an example system in which an example content presentation device constructed in accordance with the teachings of this disclosure is implemented.

Many different kinds of media content, such as audio, visual, and audio-visual content are presented to individuals every day. The presentation of media content to the individual can result in a biologically based response in the individual, which can be used to determine a mental state of the user. For example, a user may be frustrated or confused by media content displayed by a website, including the web site interface, a game, etc. Data related to a particular determined mental state of a user may be used, for example, in marketing applications. For example, if a user exhibits a biological response indicative of frustration caused by a website design, the user may be less likely spend time on the website and purchase products from the business owner of the website. Thus, market researchers could use the information about determined mental states of users to adapt the website to provide a more enjoyable experience to a user and potential consumer as indicated by positive mental or emotional states detected through the biological responses. Users having enjoyable and pleasant experiences are more likely to spend more time on a website and may be more likely to purchase products and/or services. In some examples, the media content (e.g., the website) may adapt automatically based on the determined mental state of the individual.

Example apparatus and methods described herein adjust content (e.g., media content such as commercial advertisements, websites, videos, Internet content, etc.) presented to an individual based on a determined mental state (e.g., frustration, concentration, boredom, etc.) of the individual. The mental state of the individual is determined based on measured responses (e.g., biometric responses such as heart rate, pupil dilation, etc.) to presented content. In some examples, the responses of the individual are measured using modality sensors (e.g., sensors to measure biometric responses such as heart rate sensors, pressure sensors, facial expression detectors or facial action coding (FAC), etc.) and compared to respective thresholds to determine response classifications (e.g., high or low heart rate; high, medium, or low pupil dilation; etc.).

In some examples, the thresholds may correspond to a baseline (e.g., a threshold amount above a baseline) associated with the response of the individual over a period of time during presentation of the content. For example, the measured response of an individual over time may be used to develop a baseline of biometric response activity. In such examples, an individual may have biometric data recorded while exposed to neutral or background media (as opposed to a targeted media or stimulus). The baseline determines the level of biometric activity of the person in, for example, an inactive or uninvolved state. This determination of the baseline may be different from individual to individual because, for example, some individuals have higher resting heart rates than others or different rates of respiration, etc. A threshold is set to indicate when, for example, an individual response indicative of excitement is high enough relative to the baseline to register as a positive response. Thus, the biometric data may be compared to the individualized threshold(s) to determine a high or low classification on a moment-by-moment basis for each subject, panelist, or user. Furthermore, in this example, the baseline is used as a reference for the threshold. If the comparison of the signal (the biometric data) to the threshold is constantly resulting in a "low" or "high" classification, for example, the baseline and, in some instance also the threshold, are adjusted because the response of the individual has changed over time and is not being accurately represented or detected by the constantly "low" or "high" classification. In other words, the fluctuations or changes in the individual's response may not be detected because the measured responses consistently remain below the threshold and, therefore, the threshold and baseline are to be changed to capture the fluctuations or changes.

In another example in which the baseline is adjusted based on the measured responses, a baseline is increased when a measured response is consistently higher than the threshold because this indicates that the response of the individual has changed. In this example, the baseline is increased after a period of time (e.g., thirty seconds) to account for the shift in the response of the individual (i.e., the fluctuations of the response of the individual are better measured if the baseline and threshold are increased). For example, if an individual has a resting heart rate of 70 beats per minute (bpm) (e.g., a baseline measurement), the threshold for a "high" heart rate classification may be 75 bpm. If the individual is frustrated, the heart rate may rise by, for example, approximately 10 bpm and, thus, be consistently classified as "high." In this example, when the baseline is held at 70 bpm and the threshold is held at 75 bpm, the fluctuations of the heart rate between 77 bpm and 85 bpm are not detected because the entire signal between 75 bpm and 85 bpm is registered as "high." Thus, changing the baseline and the threshold to more accurately represent the new baseline heart rate of the individual enables the fluctuations at the higher heart rate range to be classified as high or low with respect to the new baseline and threshold.

Additionally or alternatively, the baseline and/or threshold may be changed based on the task being performed by the individual. For example, a simple task (e.g., shopping for a toothbrush) may result in little or no change to the baseline and/or threshold, but a more complex task (e.g., configuring a car) may result in a larger change to the baseline and/or threshold. In some examples, the length of time the task is estimated to take may affect the adjustment of the baseline and/or threshold.

The response classifications measured during a first time frame may be combined to determine a mental classification (e.g., concentration, frustration, confusion, etc.). For example, the response classifications of high GSR, high pupil dilation, high negative FAC, and low positive FAC may indicate, when combined, that the individual is actively engaged and has a mental classification of frustration. In some examples, the mental classification is determined by, for example, combining response classifications corresponding to responses measured by different modality sensors (e.g., two or more different sensors). For example, a low GSR response, a low pupil dilation, a low negative FAC, and a low positive FAC may be combined to indicate a mental classification of low and/or no engagement (boredom). In some examples, a second mental classification is determined based on additional responses measured during a second time frame. A mental state is designated if consecutive mental classifications are similar (e.g., the mental state is designated based on a degree of similarity between consecutive mental classifications). In some examples, the mental state indicates a reaction of the individual to the presented content (e.g., frustration, confusion, etc.). In such examples, the content is adjusted or new content (e.g., second content), different from the content originally presented (e.g., first content), is presented to the individual to increase the positivity level of the reaction.

In the examples disclosed herein, the responses are measured during overlapping time frames to ensure that no peak measurements (e.g., a peak galvanic skin response (GSR) measurement) are missed. For example, the first time frame begins when the content is presented to the individual and the second time frame begins prior to an end of the first time frame. In some such examples, each time frame has a duration of four seconds and the second time frame begins one second after the first time frame begins. In conventional methods in which discrete windows are used, a peak that occurs at the end of one window and into the next may be lost.

In some examples, the response classifications are combined in time segments that include multiple overlapping time frames. For example, if each time frame has a duration of four seconds, the time segments may have a duration of two seconds. In such examples, the time segments include responses from up to four different time frames. In some examples, a mental classification is determined for each time segment based on the response classification corresponding to the respective time segments. In some such examples, the mental state is designated if the mental classifications for consecutive time segments (e.g., two or more consecutive segments) are similar. Alternatively, no mental state is designated if no consecutive mental classifications are similar.

Disclosed in some examples herein, are methods to adjust content presented to an individual. The example method includes measuring, via a first modality sensor, a first response of the individual to first content during a first time frame and determining a first response classification based on a first comparison of the first response and a first threshold. The example method also includes measuring, via a second modality sensor, a second response of the individual to the first content during the first time frame and determining a second response classification based on a second comparison of the second response to a second threshold. In addition, the example method includes determining a first mental classification of the individual based on combining the first response classification and the second response classification and determining a first baseline during the first time frame, at least one of the first threshold or second threshold based on the first baseline. The example method includes measuring, via the first modality sensor, a third response of the individual to first content during a second time frame and measuring, via the second modality sensor, a fourth response of the individual to the first content during the second time frame. In addition, the method includes adjusting the first baseline to a second baseline based on at least one of the third response or the fourth response in the second time frame, adjusting at least one of the first threshold to a third threshold or second threshold to a fourth threshold based on the second baseline, determining a third response classification based on a third comparison of the third response and the third threshold, and determining a fourth response classification based on a fourth comparison of the fourth response and the fourth threshold; determining a second mental classification of the individual based on combining the third response classification and the fourth response classification. Other aspects of the example method include determining a mental state of a user based on a degree of similarity between the first mental classification and the second mental classification, and at least one of modifying the first content to include second content or replacing the first content with second content based on the mental state.

In some examples, the first modality sensor includes a galvanic skin response sensor. Also, in some examples, the second modality sensor includes a pupil dilation sensor.

In some examples, the method also includes generating a cognitive load index based on data from the pupil dilation sensor. The cognitive load index is representative of how much of a maximum information processing capacity of the individual is being used.

In some example methods, the second time frame partially overlaps the first time frame.

In some examples, the method includes measuring, via a third modality sensor, a fifth response of the individual to the first content during the first time frame and determining a fifth response classification based on a fifth comparison of the fifth response and a fifth threshold, the first mental classification of the individual based on combining the first response classification and the second response classification further with the fifth response classification. The method also includes measuring, via the third modality sensor, a sixth response of the individual to the first content during the second time frame, and determining a sixth response classification based on a sixth comparison of the sixth response and the fifth threshold, the second mental classification of the individual based on combining the third response classification and the fourth response classification further with the sixth response classification.

In some examples, the third modality sensor includes a facial action coding sensor. Also, in some examples, the third modality sensor includes an eye tracking sensor.

Also, in some examples disclosed herein, the second content is to increase a positivity level of the mental state. In addition, in some examples, the second content is to at least one of induce a purchase or increase a total spend amount on a purchase.

Also disclosed herein are example systems including, a system that includes a first modality sensor, a second modality sensor, and a processor. In the example system, the processor is to measure, via the first modality sensor, a first response of an individual to first content during a first time frame and determine a first response classification based on a first comparison of the first response and a first threshold. The example processor also is to measure, via the second modality sensor, a second response of the individual to the first content during the first time frame, and determine a second response classification based on a second comparison of the second response to a second threshold. The example system also uses the processor to determine a first baseline during the first time frame, at least one of the first threshold or second threshold based on the first baseline and determine a first mental classification of the individual based on combining the first response classification and the second response classification. In addition, the processor is to measure, via the first modality sensor, a third response of the individual to first content during a second time frame, measure, via the second modality sensor, a fourth response of the individual to the first content during the second time frame, adjust the first baseline to a second baseline based on at least one of the third response or the fourth response in the second time frame, and adjust at least one of the first threshold to a third threshold or the second threshold to a fourth threshold based on the second baseline. Other determinations are also made by the example processor including, for examples, determining a third response classification based on a third comparison of the third response and the third threshold, determining a fourth response classification based on a fourth comparison of the fourth response to the fourth threshold, determining a second mental classification of the individual based on combining the third response classification and the fourth response classification, and determining a mental state of a user based on a degree of similarity between the first mental classification and the second mental classification. In addition, the example system uses the processor to at least one of modify the first content to include second content or replace the first content with second content based on the mental state.

Also disclosed herein are tangible computer readable storage media comprising instructions that, when executed, causes a processor of a content presentation device to at least measure, via a first modality sensor, a first response of an individual to first content during a first time frame, determine a first response classification based on a first comparison of the first response and a first threshold, measure, via a second modality sensor, a second response of the individual to the first content during the first time frame, and determine a second response classification based on a second comparison of the second response to a second threshold. In these examples, the instructions further cause the machine to determine a first baseline during the first time frame, at least one of the first threshold or second threshold based on the first baseline, and determine a first mental classification of the individual based on combining the first response classification and the second response classification. In addition, executing the instructions also causes the machine to measure, via the first modality sensor, a third response of the individual to first content during a second time frame, measure, via the second modality sensor, a fourth response of the individual to the first content during the second time frame, adjust the first baseline to a second baseline based on the third response or the fourth response in the second time frame, and adjust at least one of the first threshold to a third threshold or the second threshold to a fourth threshold based on the second baselines. Furthermore, in this example, the machine is caused by the executed instructions to determine a third response classification based on a third comparison of the third response and the third threshold, determine a fourth response classification based on a fourth comparison of the fourth response to the fourth threshold, determine a second mental classification of the individual based on combining the third response classification and the fourth response classification, and determine a mental state of a user based on a degree of similarity between the first mental classification and the second mental classification. Also, in this example, the machine is to at least one of modify the first content to include second content or replace the first content with second content based on the mental state.

Further disclosed herein are systems such as an example system that includes a first modality sensor to measure a first response of an individual to first content during a first time frame. The example system also includes a second modality sensor to measure a second response of the individual to the first content during the first time frame. The first modality sensor is to measure a third response of the individual to first content during a second time frame, and the second modality sensor is to measure a fourth response of the individual to the first content during the second time frame. The example system includes a response classifier to determine a first response classification based on a first comparison of the first response and a first threshold and determine a second response classification based on a second comparison of the second response to a second threshold. In addition, the example system includes a baseline generator to determine a first baseline during the first time frame, at least one of the first threshold or second threshold based on the first baseline and adjust the first baseline to a second baseline based on at least one of the third response or the fourth response in the second time frame. The baseline generator also is to adjust at least one of the first threshold to a third threshold or the second threshold to a fourth threshold based on the second baseline. In addition, the response classifier is to further determine a third response classification based on a third comparison of the third response and the third threshold and determine a fourth response classification based on a fourth comparison of the fourth response to the fourth threshold. The example system also includes a mental classifier to determine a first mental classification of the individual based on combining the first response classification and the second response classification and determine a second mental classification of the individual based on combining the third response classification and the fourth response classification. The mental classifier also is to determine a mental state of a user based on a degree of similarity between the first mental classification and the second mental classification. The example system also includes a content modifier to at least one of modify the first content to include second content or replace the first content with second content based on the mental state.

In some examples, the system further includes a third modality sensor to measure a fifth response of the individual to the first content during the first time frame and measure a sixth response of the individual to the first content during the second time frame. Also, in such example systems, the response classifier is to determine a fifth response classification based on a fifth comparison of the fifth response and a fifth threshold, and the mental classifier is to base the first mental classification of the individual on combining the first response classification and the second response classification further with the fifth response classification. In addition, the response classifier is to determine a sixth response classification based on a sixth comparison of the sixth response and the fifth threshold, and the mental classifier is to base the second mental classification of the individual on combining the third response classification and the fourth response classification further with the sixth response classification.

Turning now to the figures, FIG. 1 is a schematic illustration of an example system 100 in which an example content presentation device 102 is implemented. In some examples, the example system 100 is implemented in a laboratory environment for monitoring an individual 104. In other examples, the system 100 may be implemented in other environments including, for example, a public location or a private residence.

In the illustrated example system 100, the content presentation device 102 is a desktop computer. In other examples, the content presentation device 102 may be any device suitable to present media content to an individual 104, such as a television, a radio, an Internet-streamed audio source, a workstation, a kiosk, a laptop computer, a tablet computer, an e-reader, a smartphone, etc. The example content presentation device 102 presents media content to the individual 104 that includes audio, visual, and/or audiovisual content. In some examples, the content is advertisement(s) and/or entertainment. Also, in some examples, the content is interactive, such as a video game, live interaction, or an Internet experience (e.g., a website). The example content presentation device 102 includes a display 106 and/or an audio output 108 (e.g., speakers, a headset) to present the media content to the individual 104. In some examples, the display 106 and/or the audio output 108 enables the individual 104 to interact with the content presentation device 102. The content presentation device 102 includes one or more of a keyboard 110, a mouse 112, a touchscreen, a microphone, a remote control, etc. to facilitate an interaction between the individual 104 and the content presentation device 102.

In some examples, the content presentation device 102 is used to measure and/or record self-reported responses, such as responses to computer generated surveys, text input, and/or audio responses. Self-reported measurements include, but are not limited to, survey responses to items such as perception of the experience, perception of the usability or likeability of the experience, level of personal relevance to user, attitude toward content or advertising embedded in the content, intent to purchase a product, game, or service, and changes in responses from before and after testing.

In some examples, the input devices (e.g. the mouse 112 and/or keyboard 110 and/or other input devices) include sensors (e.g., biometric sensors, pressure sensors) to measure a response of the individual 104. For example, interactive content is presented to the individual 104 according to a predefined program or sequence biometric response data is recorded and synchronized or mapped to the content presentation to indicate what biological response the individual 104 had to what portion of the presentation.

As shown in FIG. 1, the additional input devices of the example system 100 include one or more modality sensors, such as sensors 114, 116, 118, to monitor a reaction of the individual 104 to the presented content. In some examples, the modality sensors 114, 116, 118 are communicatively coupled to the example content presentation device 102. Alternatively, one or more of the modality sensors 114, 116, 118 are integrated with the example content presentation device 102. The modality sensors include one or more of a camera 114 and/or biometric sensors, such as biometric sensing clothing 116 and a biometric sensing bracelet 118. In some examples, the camera 114 is a video camera and/or an infrared camera. The modality sensors 114, 116, 118 are operative to measure, for example, any combination of eye tracking responses, behavioral responses, and/or other biological responses. In some examples, eye tracking responses include pupil dilation, saccadic motion, gaze location (e.g., direction of attention) and duration, and iris size. In some examples, behavioral responses include facial expressions, levels of vocalized emotion (e.g., measure of stress of the individual 104) and movement. The detected facial expressions express discrete emotions on the face, such as joy, surprise, confusion, sadness, etc. In some examples, the biological responses include heart rate (HR) (e.g., camera-based heart rate measurement), galvanic skin response (GSR) (a measure of skin conductivity), neural activity (EEG), respiration, blood flow in the prefrontal cortex (detected by near infrared spectroscopy), activity in specific brain areas (e.g., as determined by functional MRI), skin temperature, other body temperatures, blood pressure, EMG, etc.

In some examples, the measured response data is linked and/or synchronized with the content presentation using time stamps and/or event windows. For example, the presentation is divided into event windows based on specific tasks or activities that are included in the interactive content presented to the individual 104, and the measured response data is associated with the event windows based on the tasks or activities. In some examples, each task or activity has one or more event windows associated with the task or activity. Additionally, each event window can be the same or a different duration of time as the other event windows.

The one or more modality sensors 114, 116, 118 and/or the content presentation device 102 are in communication with a server 120 via a wired or wireless network 122. In some examples, the sensors 114, 116, 118 are coupled to the network 122 via the content presentation device 102. In some examples, the network 122 uses communication technologies such as RS-232, Ethernet, Wi-Fi, Bluetooth or ZigBee. The server 120 additionally is in communication with a results analyzing device 124, which is illustrated as a desktop computer but other devices may be used as noted herein. Additionally or alternatively, more than one communication technology is used at the same time, including wired components (e.g., Ethernet, digital cable, etc.) and wireless components (Wi-Fi, WiMAX, Bluetooth, etc.) to connect the sensors 114, 116, 118 and/or other computer system components to the server 120.

Alternatively or additionally, the results analyzing device 124 includes any device suitable to analyze data collected by the content presentation device 102 and/or the modality sensors 114, 116, 118, including a workstation, a kiosk, a laptop computer, a tablet computer, and a smartphone. In some examples, the results analyzing device 124 receives input from a reviewer 126 related to the results corresponding to the individual 104. The results are transmitted to, for example, the server 120, a second server, and/or an additional computing device. Alternatively, the results include a generated report 128 (e.g., a hard or a soft copy) distributed to, for example, a client. In some examples, the results analyzing device 124 is integrated with the content presentation device 102 to determine moment-to-moment, event-to-event or total level of emotion and cognition classifiers and provides the results to the server 120. Analyzing the results using the results analyzing device 124 prior to transmitting the results the server 120 decreases the amount of data transferred, resulting in faster data processing and lower transmission bandwidth requirements to increase the operating efficiency of the system.

As used herein, the phrase "in communication," including variances thereof, encompasses direct communication and/or indirect communication through one or more intermediary components and does not require direct physical (e.g., wired) communication and/or constant communication, but rather additionally includes selective communication at periodic or aperiodic intervals, as well as one-time events.

Figure 2:
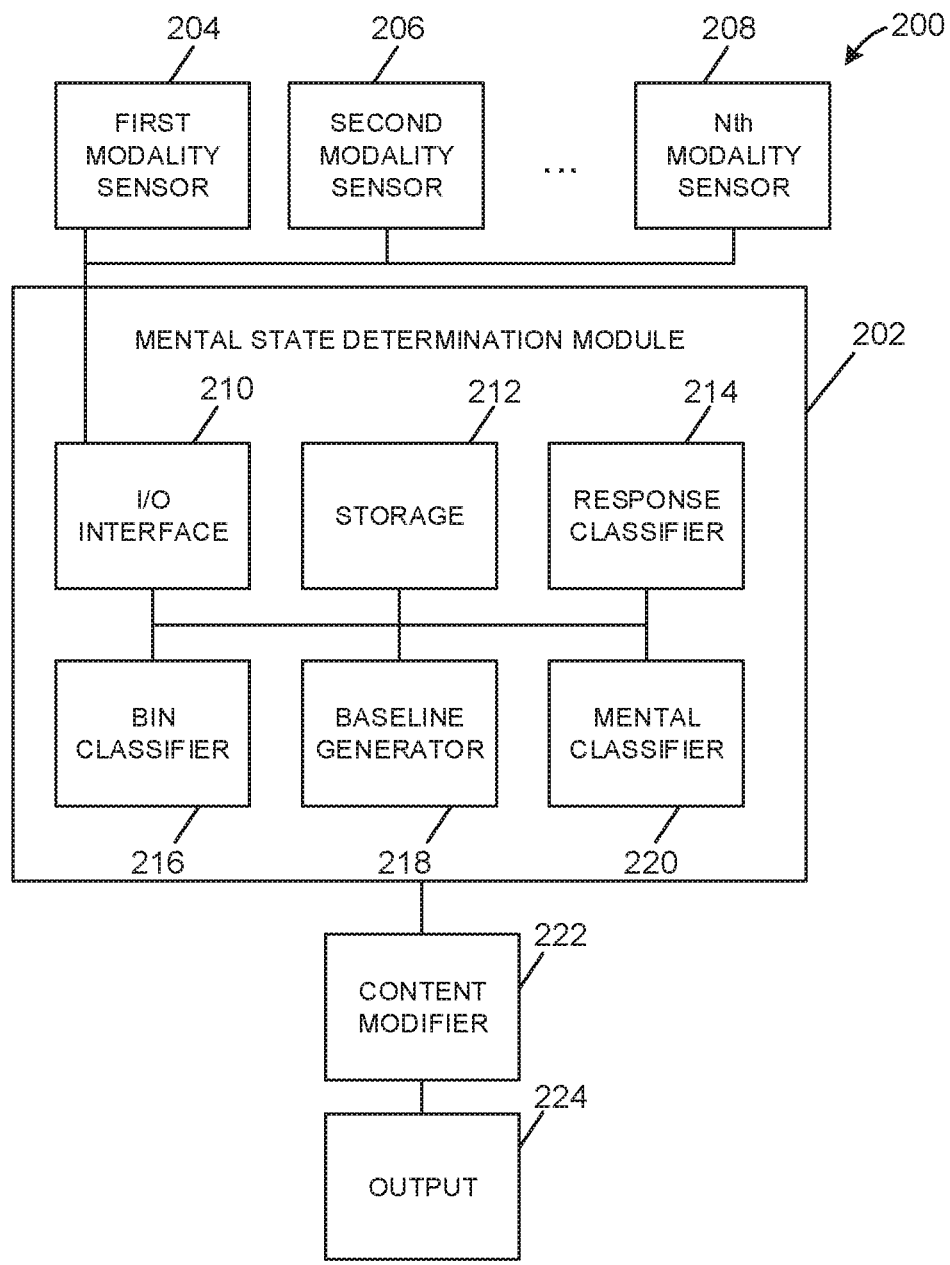
FIG. 2 is a block diagram of an example system that may be used to implement one or more of the example devices of the example system of FIG. 1.

FIG. 2 is a block diagram of an example system 200 that may be used to implement one or more of the example devices of the example system 100 of FIG. 1. The example system 200 includes a mental state determination module 202. The example mental state determination module 202 determines a mental state of the individual 104 based on measured responses to content presented to the individual 104.

The example mental state determination module 202 is communicatively coupled to a plurality of modality sensors including, for example, a first modality sensor 204, a second modality sensor 206, and an Nth modality sensor 208. In some examples, the first modality sensor 204, the second modality sensor 206, and the Nth modality sensor 208 correspond to any of the camera 114, the biometric sensing clothing 116, and the biometric bracelet 118 of FIG. 1. Alternatively, the first, second, and Nth modality sensors 204, 206, and 208 include any sensor operative to measure at least one of an eye tracking response, a behavioral response, or a biometric response of the individual 104. Additional modality sensors may be included to measure other biometric responses of the individual.

The example mental state determination module 202 includes an input/output interface (I/O interface) 210. The example I/O interface 210 is operatively coupled to the first, second, and Nth modality sensors 204, 206, and 208 to communicate a response of the individual 104 to the example mental state determination module 202. Additionally or alternatively, the I/O interface 210 is operatively coupled to any of the display 106, the audio output 108, the keyboard 110, the mouse 112, a touchscreen, a microphone, or any other device capable of providing an output to the individual 104 and/or providing an input to the content presentation device 102. Additionally, the I/O interface 210 is in communication with the server 120 of FIG. 1 to communicate with the example results analyzing device 124 and/or any other device in communication with the server 120. For example, the I/O interface 210 receives the content to be presented to the individual 104 via communication with the server 120. Alternatively or additionally, the I/O interface 210 transmits results from the content presentation device 102 to the server 120.

In the illustrated example, the mental state determination module 202 includes storage 212 (e.g., a mass storage device) to store response data corresponding to the individual 104, content to be presented to the individual 104, and/or instructions for processing the response data. The example storage 212 is in communication with the I/O interface 210 to send and receive response data and/or media content to and/or from, for example, the first modality sensor 204, the second modality sensor 206, the Nth modality sensor 208, and/or the server 120. Alternatively or additionally, in some examples, the example storage 212 is in direct communication with one or more of the first modality sensor 204, the second modality sensor 206, the Nth modality sensor 208, and the server 120.

The example mental state determination module 202 includes a response classifier 214 to determine a response classification of measured response data received from one or more of the first, second, and Nth modality sensors 204, 206, and 208. The example response classifier 214 determines the response classification (e.g., high or low heart rate; high or low GSR; high, medium, or low pupil dilation; etc.) by, for example, comparing the measured response to a threshold. In some examples, each measured response corresponding to one of the modality sensors 204, 20, 208 is compared to a different threshold (e.g., a respective threshold) based on, for example, different biological characteristics of the signals and responses for the respective modality. The threshold is determined based on, for example, an average value of the measured response during an initial time period (e.g., a baseline). In some examples, the response classifier 214 determines which responses are most likely to be relevant to the mental state of the individual 104 from the available response measurements. In some examples, the selection of responses relevant to the mental state is confirmed using a research methodology. For example, a hypothesis is generated, a study is created, participants are recruited, data is collected and analyzed, and a conclusion is drawn. Additionally or alternatively, in some examples, a statistical model of the contributions of each of the responses is created to select the responses with the greatest relevance to the mental state of the individual 104. The example statistical model may be used to classify responses and/or determine a range for characterization of responses using an assumed statistical probability density. In some examples, the statistical model may form the bases for classification barriers and determine if one mental state is more likely than another.

The example mental state determination module 202 includes an example bin classifier 216. In some examples, the bin classifier 216 creates one or more bins in which to place each response based on the respective thresholds and/or a baseline. For example, each response (e.g., the measurement from each modality sensor 204, 206, 208) is sorted into a bin (e.g., a high bin, a low bin) based on the comparison to the threshold, and the one or more bins may be created based on the baseline. In some examples, the bin classifier 216 determines binning criteria based on the response measurement and/or sensor measuring the response being binned. For example, for GSR binning, the baseline (e.g., the binning criteria) is determined by calculating a mean GSR for a portion of the response measurement. Example GSR bins include a high bin (e.g., 50% increase above the mean GSR) and a low bin (e.g., 25% increase above the mean GSR). Additionally or alternatively, binning criteria for an HR response measurement is determined by a change in absolute beats-per-minute (bpm) within a two-second window. Example HR bins include a high bin (e.g., increase of 12-15 bpm) and a low bin (e.g., decrease of 12-15 bpm).

Additionally or alternatively, the bin classifier 216 divides some responses, such as facial responses, into positive and negative categories prior to sorting the response into a high or low bin. In such examples, a database of facial responses is created from participants during testing to determine relative baseline(s) for positive and negative expressions. Example facial response bins include a high bin (e.g., one standard deviation in probability of coding an expression as positive/negative above the standard deviation and the opposite response is low (i.e., to code high positive FAC, negative FAC response must be low)) and a low bin (e.g., one standard deviation decrease in probability, below data baseline, of coding an expression as positive/negative).

In some examples, the bin classifier 216 creates an intermediate bin for response measurements, such as pupil dilation. For example, pupil dilation binning includes determining the baseline based on a function of change from mean pupil dilation during some portion of the measured response. In some examples, pupil dilation binning includes a medium bin to capture times when the individual 104 is cognitively engaged, but not necessarily heavily concentrating, frustrated, or bored. Example pupil dilation bins include a high bin (e.g., mean dilation plus at least one half standard deviation), a medium bin (e.g., within one half standard deviation of the mean), and a low bin (e.g., mean dilation minus at least one half standard deviation). In some examples, the response classifier 214 uses the bins to determine the response classification of a response and/or places the responses in bins based on the comparison of the response to the threshold. In some such examples, the response classifier 214 and the bin classifier 216 work cooperatively to place responses in an appropriate bin based on the response classification and/or the comparison of the response to the threshold or baseline.

Typically, all responses are weighted equally when determining the mental state of the individual 104 (e.g., if three responses were measured, each response contributes to the mental state 33%). In some examples, the responses are weighted by adjusting the contribution of one or more responses to the overall results to be more or less than the contribution of other responses. For example, if one of the modality sensors 204, 206, 208 is not measuring data for all or part of the content presentation, the weighting of the contribution of each response is adjusted (e.g., if only two responses are measured at a given time, each response contributes to the mental state 50%). As more response data is collected and/or as the reaction to the presented content changes, the weights of the responses contributions can be adjusted to improve accuracy of the results (e.g., the response classification, a mental classification, the determined mental state).

The example mental state determination module 202 includes an example baseline generator 218. In some examples, the baseline generator 218 determines an initial baseline using a baselining procedure. For example, response measurements are not binned (e.g., classified) for an initial time period such as, for example, thirty seconds. The length of the initial time period may vary based on a task being performed by the individual. In some examples, neutral content is presented to the individual 104 during the initial time period. During the initial time period, a representative value (e.g., a mean value, a standard deviation, etc.) is determined by the baseline generator 218, for example, for the responses related to each sensor and are used as the initial baseline. In such examples, responses are compared to the initial baseline and/or a respective one of the thresholds. Additionally or alternatively, after the initial time period, the baseline is periodically adjusted based on the measured responses. For example, the baseline generator 218 re-evaluates the baseline for each baseline time period (e.g., thirty seconds) and adjusts the baseline based on the response. Alternatively or additionally, the baseline time period is the same as the first time frame. For example, if a user's GSR is above the mean (e.g., sorted in the high bin) for a period of time and then drops below the mean, the baseline determiner 218 adjusts the baseline in response to the drop in the GSR measurement to establish a new baseline. Thus, the baseline determiner 218 automatically adjusts the baseline corresponding to each response measurement in response to the occurrence of relevant events.

Automatically adjusting the baseline as the response of the individual changes and/or develops increases the accuracy of the determined mental state. For example, determining the mental state based on a single and/or constant baseline may not detect fluctuations or changes in the response of the individual (e.g., drop in heart rate after a period of higher heart rate) because the response (e.g., heart rate) may still be higher than the initial baseline and, thus, classified as high. The failure to detect these fluctuations or changes may result in an incorrect classification of the response.

In addition, there are many advantages to adjusting the baseline. For example, if an individual is experiencing frustration with a website, which is detected based on the individual's GSR being above a threshold relative to the baseline, and there may be a modification of the content to alter the mental state of the user to a more enjoyable experience. The modification of the content may begin to work to bring the individual to a less frustrated state. However, at the initial stages of the change, the individual's GSR may remain above the threshold relative to the baseline, though the individual's mental state is changing in accordance with the goals of the modified content. However, these changes may go undetected based on the level of GSR compared to the threshold relative to the baseline. Whereas, an adjusted baseline would change the threshold trigger, and enable detection of the GSR (in this example) moving across the threshold and provide indication that the content modification is effective. Therefore, the content modification can continue to bring the individual into the desired mental state. In addition, where the baseline is moved and the threshold has not been triggered though content has been modified, the operator or website owner would know that the content modification did not work (or did not work fast enough) or that a secondary baseline adjustment may be needed for a finer detection of biometric responses and/or mental classification and state changes.

In some examples, a running window implementation is used. In some such examples, the running windows include overlapping time windows (e.g., four-second windows). In some examples, the responses are measured using overlapping windows to avoid inaccuracies and/or missed events in the collected data. For example, GSR measurements typically peak at approximately four to five seconds, which can be missed or misinterpreted using non-overlapping time windows to measure GSR responses. In the example disclosed herein, the time windows each have a duration of four seconds and begin in one-second increments. In other examples, any other suitable or desired time duration(s) and/or increment(s) may be used. In some examples, the response is binned and/or a response classification is determined for each of the time windows.

The example mental state determination module 202 also includes an example mental classifier 220. The example mental classifier 220 determines mental classifications related to the measured responses (e.g., raw data from the modality sensors) and/or the response classifications (e.g., response data that is classified based on a threshold). In some examples, the mental classifications are determined by combining response classifications (e.g., high heart rate and low GSR) corresponding to one or more modality sensors 204, 206, and 208. In the illustrated example, the response classifications are combined in time segments shorter than the time windows (e.g., two seconds) and include the response classifications determined for each time window related to the time segment.

Figure 3:
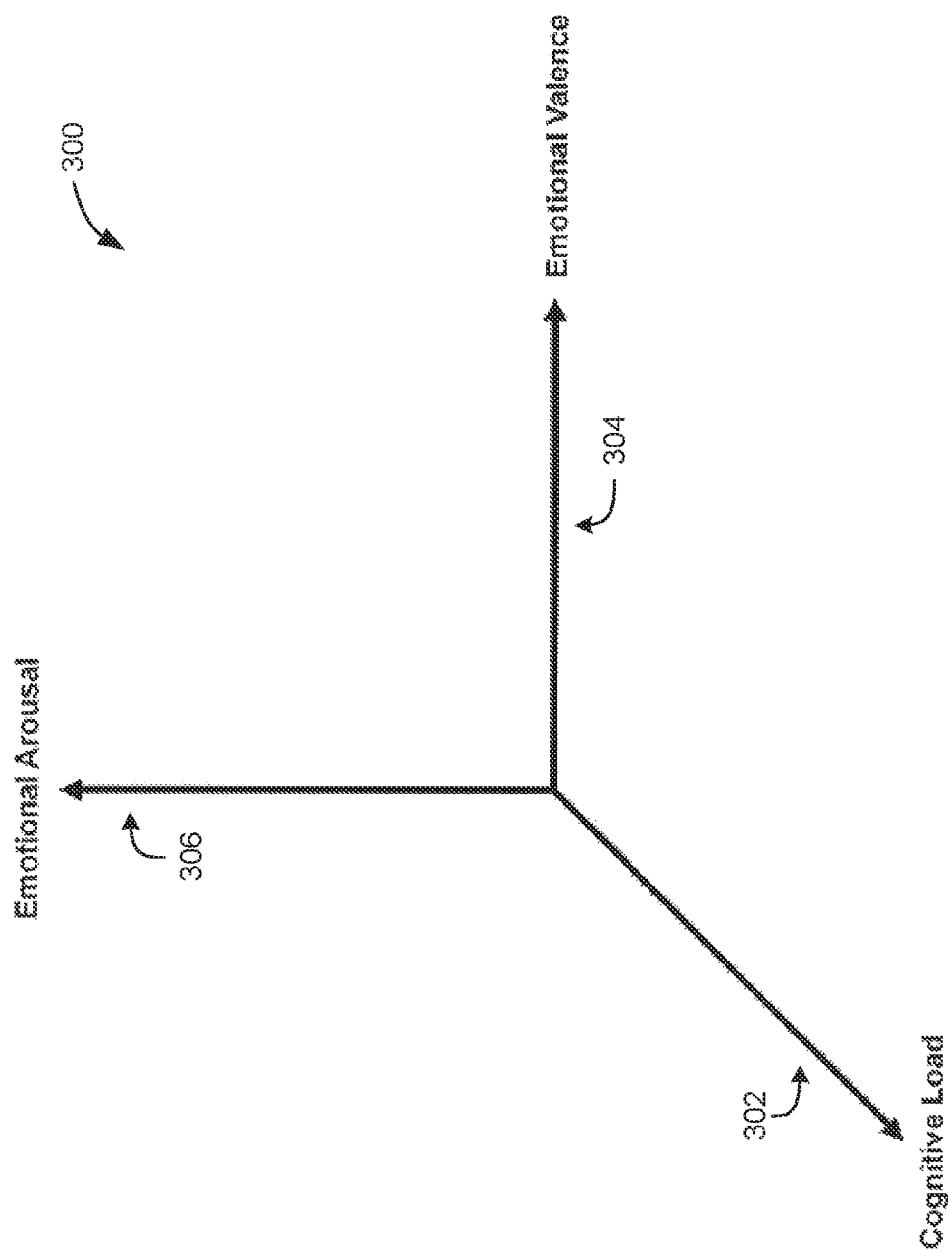
FIG. 3 is a representation of an example mental classification grid that may be used by the example content presentation device of FIGS. 1 and/or 2 to adjust content presented to an individual.

In some examples, the mental classifier 220 uses a mental classification grid, such as the example mental classification grid 300 in FIG. 3, to determine a mental classification for a time segment based on the one or more response classifications associated with the time segment. FIG. 3 is a representation of an example mental classification grid 300 that may be used by the example systems of FIGS. 1 and/or 2 to adjust content presented to an individual 104. In the illustrated example, the mental classification grid 300 includes three axes (e.g., cognitive load 302, emotional valence 304, and emotional arousal 306). In other examples, the classification grid 300 includes more than three axes (e.g., four axes, five axes, etc.).

In some examples, one of the axes used to determine a mental classification of an individual is cognitive load. The cognitive load axis 302 refines the classifications and/or the emotional valence 304 and the emotional arousal 306. The cognitive load is determined based on biological measures, such as measurements of pupil dilation. A cognitive load index represents the maximum amount of information the individual 104 can process at a given time. Cognitive load 302 is quantified based on the index to represent how much information the individual 104 is processing at a given time. Including cognitive load 302 as an axis in the example mental classification grid 300 provides significant functionality. Each individual 104 is determined to have a maximum information processing capacity. Comparing the cognitive load of the individual 104 during a period of time to the cognitive load index provides information related to the mental state of the individual 104. For example, if the individual 104 exhibits a high cognitive load index and a low emotional index, the determined mental state is concentration. In some examples, the emotional index is based on the emotional valence 304 and/or the emotional arousal 306. Thus, the use of cognitive load 302 allows the example mental state determination module 202 and/or the mental classifier 220 to distinguish between mental states such as frustration, confusion, and concentration.

Figure 4:
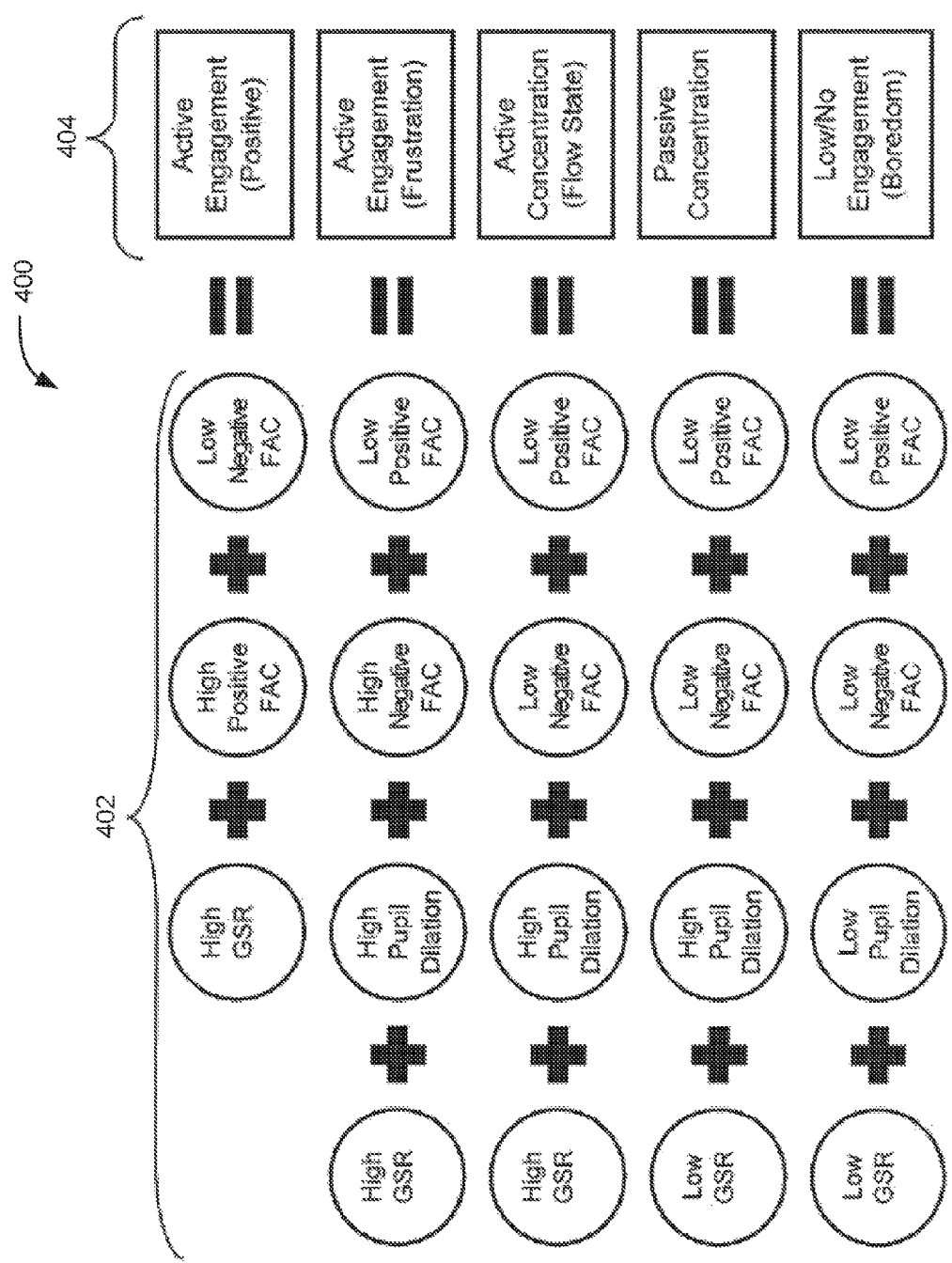
FIG. 4 is a representation of an example mental classification matrix that may be used by the example content presentation device of FIGS. 1 and/or 2 to adjust content presented to an individual.

Additionally or alternatively, the mental classifier 220 uses a mental classification matrix, such as the example mental classification matrix 400 of FIG. 4, to determine a mental classification based on one or more response classifications. FIG. 4 is a representation of an example mental classification matrix 400 that is used by the example system of FIGS. 1 and/or 2 to adjust content presented to an individual 104. The example classification matrix 400 represents an example method of combining example response classifications 402 to determine example mental classifications 404. In the illustrated example mental classification matrix 400, the example response classifications 402 represent possible combinations of response classifications for a response measurement. For example, a first response measurement may occur during a first time window (e.g., time window 502 of FIG. 5) and correspond to high GSR, high positive FAC, and low negative FAC, which are combined by, for example, the example mental classifier 220 to produce the mental classification of active engagement (positive). Other mental classifications are created by combining different response classifications 402 for similar response measurements.

In the illustrated example, response classifications 402 that can be combined by the mental classifier 220 to create other mental classifications 404 (e.g., active engagement (frustration), active concentration (flow state), passive concentration, low/no engagement (boredom), etc.) include one or more response classifications 402 different than the response classifications 402 combined to provide an active engagement (positive) mental classification 404. The example response classifications 402 in the example mental classifications matrix 400 include response classifications 402 corresponding to measurements (e.g., GSR, pupil dilation, FAC, etc.) using the sensors (e.g., the first modality sensor 204, the second modality sensor 206, the Nth modality sensor 208, the camera 114, the biometric sensing clothing 116, the biometric sensing bracelet 118, etc.). In other examples, the example response classifications 402 correspond to additional and/or alternative sensor measurements (e.g., HR, EEG, pupil tracking, etc.). The example mental classification matrix 400 illustrated in FIG. 4 represents only a portion of the potential response classifications 402 and/or mental classifications 404 that can be designated as the mental state of the individual and, thus, the mental state and/or the mental classifications 404 are not limited to the example mental classifications 404 in the mental classification matrix 400 of FIG. 4.

Figure 5:
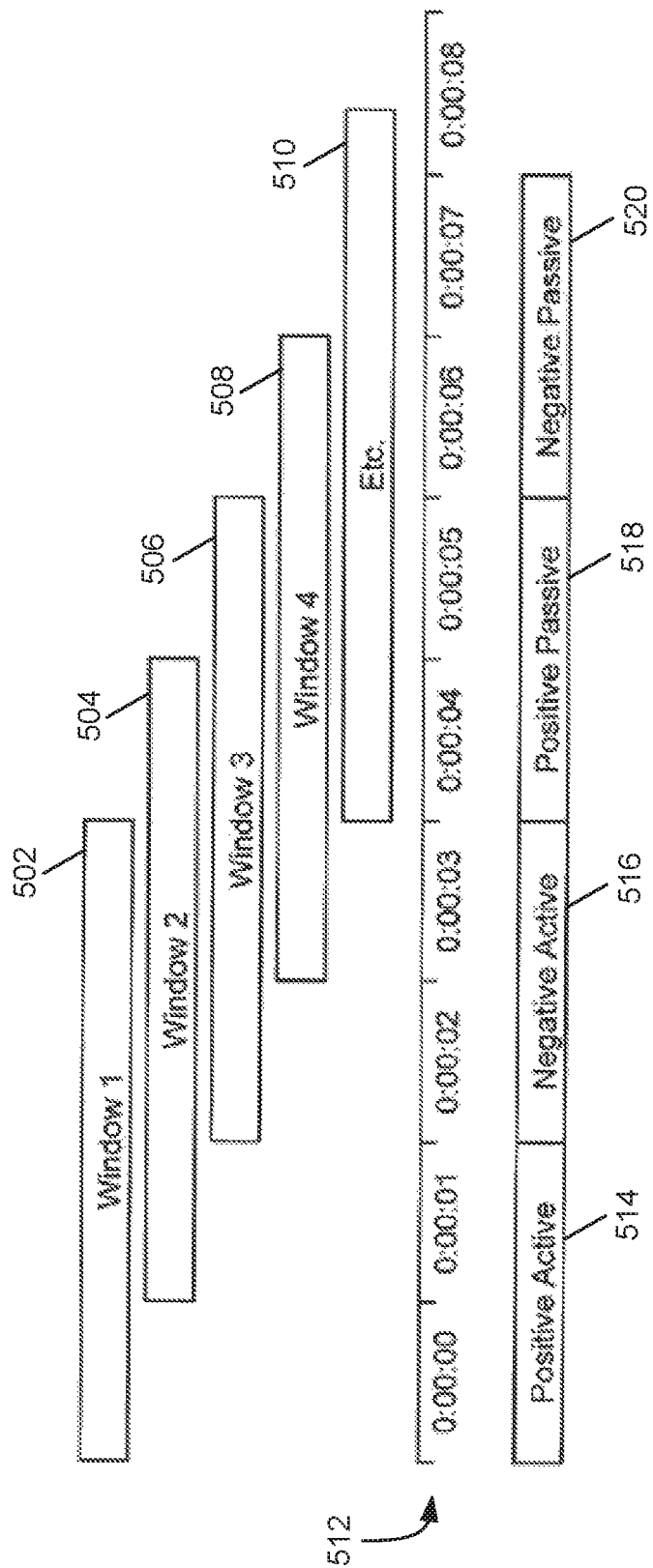
FIG. 5 is a representation of overlapping time windows that may be used by the example content presentation device of FIGS. 1 and/or 2 to adjust content presented to an individual.

FIG. 5 is a representation of overlapping time windows 502-510 used by the example system of FIGS. 1 and/or 2 to adjust content presented to an individual 104. The example time windows 502-510 correspond to response measurements from a single modality sensor such as, for example the first modality sensor 204. In some examples, the first time window 502 begins when the content is presented to the individual 104. In some examples, each of the subsequent time windows 504-510 begin one second after the previous time window (e.g., each time window 504-510 begins in a one-second interval). For example, the first time window 502 begins at time 0:00:00, as shown by the timeline 512, a second time window 504 begins at time 0:00:01, and a third time window 506 begins at time 0:00:02. Alternatively, the time windows 502-510 begin at different intervals determined based on, for example, the length of each of the time windows 502-510 and/or the length of each of the segments 514-520. In some examples, the response measurements from the other sensors (e.g., the second modality sensor 206, the Nth modality sensor 208, etc.) have time windows of the same duration as the length of the time windows 502-510. Additionally or alternatively, the time windows 502-510 correspond to a response classification for the response measurement. For example, the example response classifier 214 determines a response classification for the response measurements in each of the time windows 502-510.

In some examples, the example response classifications corresponding to time windows 502-510 are combined in two-second time segments 514-520 to determine a mental classification for each of the time segments 514-520. In some examples, the response measurements from all modality sensors 204, 206, 208 are combined during the same time segment (e.g., time segment 514) to determine a mental classification corresponding to the time segment 514. Additionally or alternatively, the time windows 502-510 falling within each of the time segments 514-520 are combined to determine the mental classification for a time segment (e.g., time segment 516). For example, the mental classification corresponding to time segment 516 is determined by combining response classifications from all time windows (e.g., the first four time windows 502-508) that at least partially overlap and/or fall within the time segment 516. In the illustrated example of FIG. 5, the time segments 514-520 include four different mental classifications (e.g., positive active, negative active, positive passive, and negative passive) and no mental state of the individual 104 is designated. Alternatively, one or more consecutive time segments include a similar mental classification (e.g., segments 514-516 are positive active) and a mental state of the individual 104 is designated based on the similar mental classification.

In some examples, the mental classifier 220 (FIG. 2) selects relevant responses (e.g., response measurements likely to be indicative of the mental state of the individual 104) used to determine the mental classification of the individual 104. In some examples, additional responses of the individual 104 are measured for the first time frame during which content is presented to the individual 104. In such examples, an additional response classification is determined based on a comparison of the additional response measured to an additional threshold. In some such examples, the additional response classification is combined with the first response classification. In such examples, the first mental classification is altered based on the additional response classification.

After the mental state determination module 202 determines the mental state of the individual 104, an example content modifier 222 determines whether to modify the content. In some examples, the content modifier 222 edits the content presented to the individual 104 based on the determined mental state of the individual 104. For example, if the mental state indicates that the individual 104 is frustrated, the content modifier 222 presents new content (e.g., second content) to the individual and/or adjusts the content to increase a positively of the mental state. In some examples, the new content includes a coupon and/or a video (e.g., a tutorial video). Alternatively, the new content is a coupon, a free gift, a suggestion, etc. In some such examples, the new content induces a purchase of a product. In other examples, the new content increases a total amount spent on a purchase.

In some examples, the new content is provided as an output 224, such as content displayed via the display 106, printed content, audio content, or any other type of media content presentable to the individual 104. In some examples, the output 224 includes response data (e.g., response classifications, mental classifications, and the determined mental state) transmitted to the server 120. In some examples, the output 224 is in communication with the server 120 and/or the content presentation device 102 via the I/O interface 210 of the mental state determination module 202.

While an example manner of implementing the system 100 of FIG. 1 is illustrated in FIG. 2, one or more of the elements, processes and/or devices illustrated in FIG. 2 may be combined, divided, re-arranged, omitted, eliminated and/or implemented in any other way. Further, the example mental state determination module 202, the example first modality sensor 204, the example second modality sensor 206, the example Nth modality sensor 208, the example I/O interface 210, the example storage 212, the example response classifier 214, the example bin classifier 216, the example baseline generator 218, the example mental classifier 220, the example content modifier 222, the example output 224, and/or, more generally, the example systems 100, 200 of FIGS. 1 and 2 may be implemented by hardware, software, firmware and/or any combination of hardware, software and/or firmware. Thus, for example, any of the example mental state determination module 202, the example first modality sensor 204, the example second modality sensor 206, the example Nth modality sensor 208, the example I/O interface 210, the example storage 212, the example response classifier 214, the example bin classifier 216, the example baseline generator 218, the example mental classifier 220, the example content modifier 222, the example output 224 and/or, more generally, the example systems 100, 200 of FIGS. 1 and 2 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example mental state determination module 202, the example first modality sensor 204, the example second modality sensor 206, the example Nth modality sensor 208, the example I/O interface 210, the example storage 212, the example response classifier 214, the example bin classifier 216, the example baseline generator 218, the example mental classifier 220, the example content modifier 222, the example output 224 and/or, more generally, the example systems 100, 200 is/are hereby expressly defined to include a tangible computer readable storage device or storage disk such as a memory, a digital versatile disk (DVD), a compact disk (CD), a Blu-ray disk, etc. storing the software and/or firmware. Further still, the example systems 100, 200 of FIGS. 1 and 2 may include one or more elements, processes and/or devices in addition to, or instead of, those illustrated in FIG. 2, and/or may include more than one of any or all of the illustrated elements, processes and devices.

Figure 6:
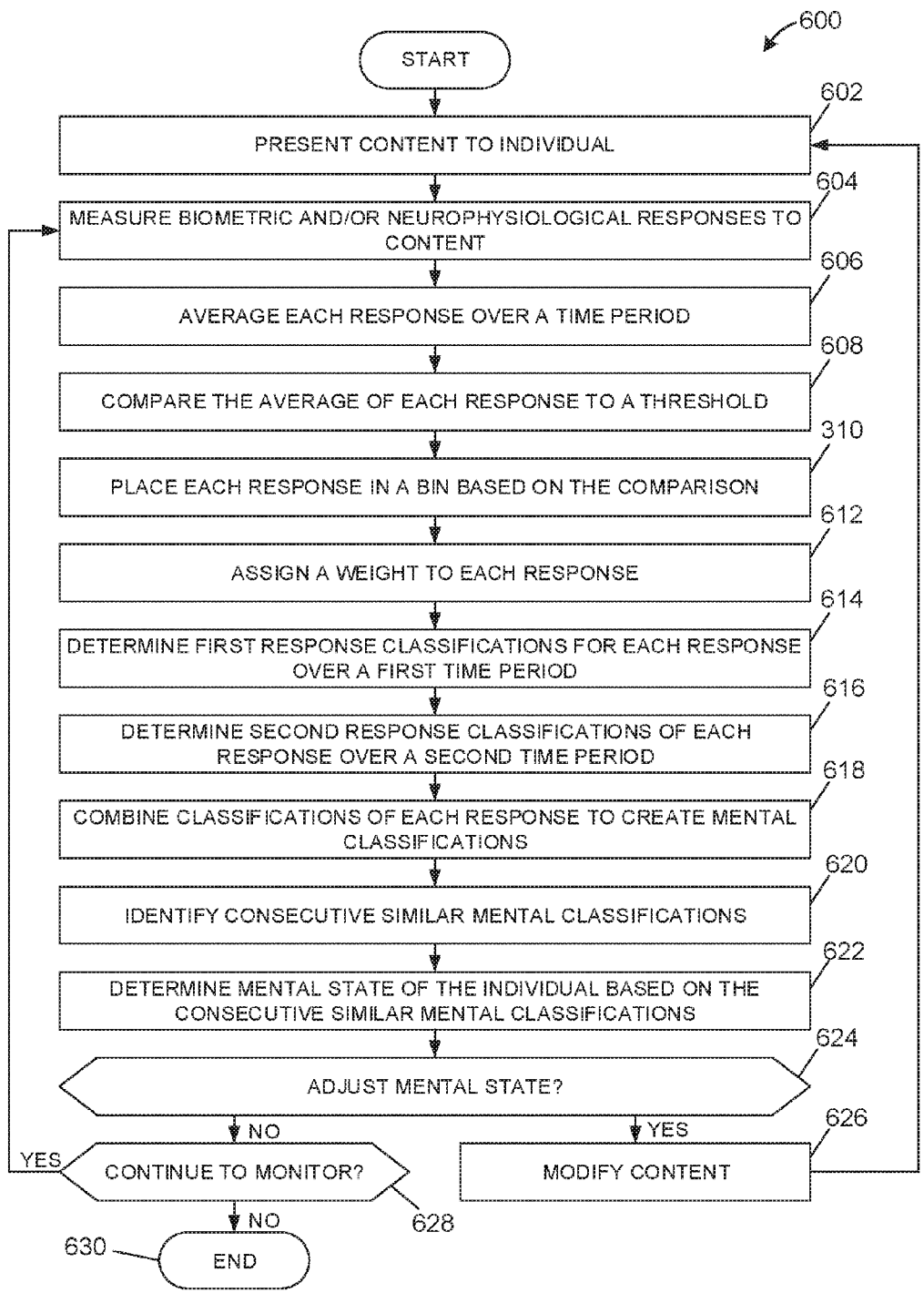
FIG. 6 is a flowchart representative of example machine-readable instructions for adjusting content presented to an individual that may be executed by the example systems of FIGS. 1 and/or 2.
Figure 7:
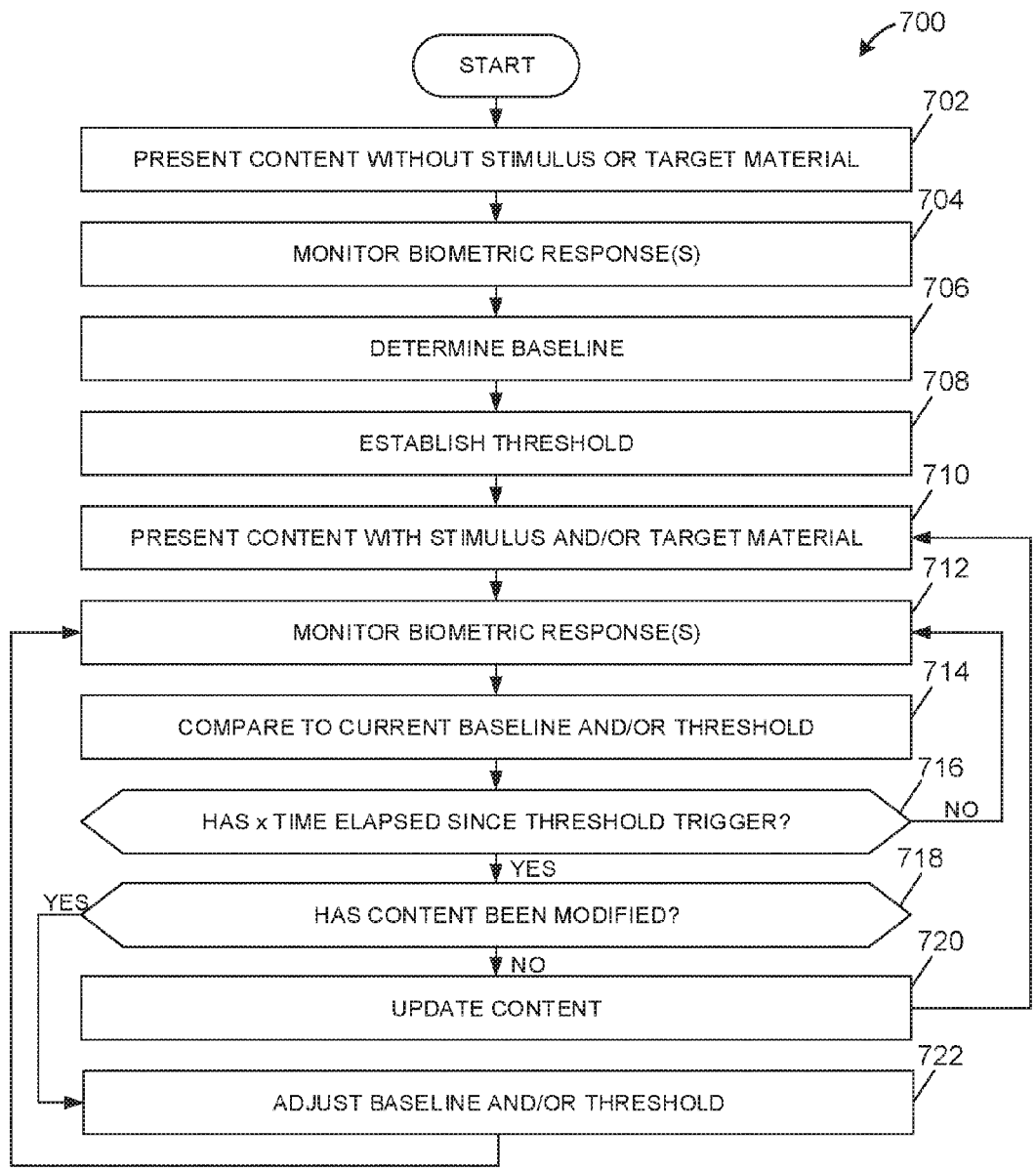
FIG. 7 is a flowchart representative of example machine-readable instructions for adjusting a baseline and/or threshold that may be executed by the example systems of FIGS. 1 and/or 2.

A flowchart representative of example machine readable instructions for implementing the systems 100, 200 of FIGS. 1 and 2 is shown in FIGS. 6 and 7. In this example, the machine readable instructions comprise a program for execution by a processor such as the processor 812 shown in the example processor platform 800 discussed below in connection with FIG. 8. The program may be embodied in software stored on a tangible computer readable storage medium such as a CD-ROM, a floppy disk, a hard drive, a digital versatile disk (DVD), a Blu-ray disk, or a memory associated with the processor 812, but the entire program and/or parts thereof could alternatively be executed by a device other than the processor 812 and/or embodied in firmware or dedicated hardware. Further, although the example program is described with reference to the flowchart illustrated in FIGS. 6 and 7, many other methods of implementing the example systems 100, 200 may alternatively be used. For example, the order of execution of the blocks may be changed, and/or some of the blocks described may be changed, eliminated, or combined.

As mentioned above, the example processes of FIGS. 6 and 7 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and transmission media. As used herein, "tangible computer readable storage medium" and "tangible machine readable storage medium" are used interchangeably. Additionally or alternatively, the example processes of FIGS. 6 and 7 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and transmission media. As used herein, when the phrase "at least" is used as the transition term in a preamble of a claim, it is open-ended in the same manner as the term "comprising" is open ended.

FIG. 6 is a flowchart representative of example machine-readable instructions 600 that may be execute to adjusting content presented to an individual 104 (using, for example, the example systems of FIGS. 1 and/or 2). The example instructions 600 begin execution when content, including audio, visual, audio-visual, and interactive content, is presented to the individual 104 via the content presentation device 102 (block 602). In an example implementation, one or more individuals is presented, via, for example, the content presentation device 102, a website including an interactive configurator. Consider, for example, the individuals using an online configurator for Adagio teas, which allows users to utilize a web interface to create custom tea blends. Alternatively, other interactive configurators could be used (e.g., Motorola MotoX Motomaker to custom design a mobile telephone, Mini auto configurator to customize an automobile, etc.). The example may also be implemented with other types of media not restricted to media intended for the purchase of customized products such as, for example, shopping for off the shelf products, gaming, entertainment, news, education, etc.

The example instructions 600 include measuring biometric and/or neurophysiological responses to content (block 604). For example, one or more of the example sensors (e.g., the camera 114, the biometric sensing clothing 116, the biometric sensing bracelet 118, and/or the first, second, and Nth modality sensors 204, 206, 208) measures the response of the individual 104 to the content, which may include a biometric response, a neurophysiological response, and/or a behavioral response. In some examples, a first response to first content is measured by the first modality sensor 204 during a first time frame and a second response to first content is measured by the second modality sensor 206 during the first time frame. Additionally, in some examples, the first modality sensor 204 measures a third response of the individual to first content during a second time frame and the second modality sensor 206 measures a fourth response of the individual to the first content during a second time frame. In the example implementation, sensors collected data related to GSR, FAC, eye tracking and pupil dilation for the individuals exposed to the Adagio tea configurator. The responses are averaged over a time period (block 606) using, for example, the response classifier 214 to average the responses (e.g., heart rate, pupil dilation, GSR, etc.) of each sensor 204, 206, 208 over a first time frame.

For example, the responses of each of the individuals were monitored for the duration of the exposure to various images, text, displays, and/or other options presented via the Adagio tea configurator. The duration included multiple time frames. The responses of the individual were averaged for each of the time frames. For example, a sensor detected FAC may detect a furrowed brow and a tight lip during a time window. These detected features could change over the duration of the time window, and an average across the window in determined.

The example instructions 600 include comparing the average of each response to a threshold (block 608). For example, the response classifier 214 compares the average response values to respective thresholds corresponding to the sensors 204, 206, 208 to classify each response (e.g., high heart rate, low heart rate, low GSR, etc.). In some examples, a first response is compared to a first threshold and a second response is compared to a second threshold. In some examples, the first threshold or the second threshold is based on a first baseline determined for a first time frame. In some such examples, the first baseline is adjusted to a second baseline based on the third response and/or the fourth response. In some examples, the first threshold is adjusted to a third threshold and/or the second threshold is adjusted to a fourth threshold. Additionally, in some examples, a third response is compared to a third threshold and a fourth response is compared to a fourth threshold.

For example, in the Adagio tea implementation described above, the individuals using the configurator may be presented with 30 images and 4 video clips to establish a baseline and/or threshold to which the responses measured during the exposure to the Adagio tea configurator are compared. The individuals' responses from one or more sensors (including for example GSR, FAC, and/or pupillary dilation) are compared to the thresholds over time. For example, the average FAC response (based on the furrowed brow and tight lip mentioned above) is compared to a threshold value related to features detected via FACs sensors to determine a relative level of, for example, furrowed brows and tight lips. In addition, the system operating the configurator may, at times, determine that a baseline and/or threshold may have to be adjusted, as described above and below with respect to FIG. 7.

Each response is placed in a bin based on the comparison (block 610). In addition, the example bin classifier 216 places each response into a respective bin (e.g., high, medium, low) based on the comparison to the threshold. The response classifier 214 determines a response classification (e.g., high GSR, low heart rate, low pupil dilation, etc.) for each response based on the comparison of the average response value(s) to the threshold(s) and/or the bin(s) in which each response is placed.

For example, the responses of the individuals using the Adagio tea configurator are placed in high or low GSR bin; high, medium, or low FAC bins; and high, medium, or low pupillary dilation bins and/or other bins relative to the biometric responses detected from the individual while presented with the configurator. For example, a low FAC bin may include negative responses such as, for example, those identifiable by furrowed brows and tight lips.

The example instructions 600 include assigning a weight to each response (block 612). For example, the response classifier 214 assigns a weight to each response corresponding to the amount each response contributes to the determined mental state of the individual 104. For example, if three response classifications are available, each response classification may be weighted as 33%. In another example implementation, each of the responses are given a weight corresponding to the contribution of each response to the determined mental state. For example, pupil dilation data can be adversely affected due to changing lighting when viewing dynamic media and, thus, the weighting for pupil dilation may be less than the weighting for each of GSR, FAC, and/or eye tracking, etc.

The example instructions 600 also determine first response classification for each response over a first time period (block 614) and second response classification of each response over a second time period (block 616). For example, the response classifier 214 of FIG. 2 may be used to provide these determinations based on the comparison of the average response to a threshold (block 608) and/or a bin (block 610) in which the response was placed. In some examples, a first response classification is determined based on a first comparison of the first response and a first threshold and a second response classification is determined based on a second comparison of the second response to a second threshold. Additionally, in some examples, a third response classification is determined based on a third comparison of the third response data to a third threshold and a fourth response classification is determined based on a fourth comparison of the fourth response to a fourth threshold.

In the Adagio tea example implementation, responses are measured over numerous time periods, and response classifications are determined for each time period by comparing the responses to relevant thresholds to detect fluctuations or changes in the response of the individual. For example, based on the comparison of the FACs data (e.g., the furrowed brows and tight lips) to the thresholds and/or bin data, it may be determined that the responses during the measured time periods if low or negative.

In this example, the instructions 600 combine classifications of each response to create a mental classification (block 618). For example, the mental classifier 220 determines a mental classification (e.g., frustration, confusion, boredom, etc.) for a time segment by combining response classifications from the first time period and/or the second time period. In some examples, a first mental classification of the individual is determined based on combining the first response classification and the second response classification. Additionally, in some examples, a second mental classification is determined based on combining the third response classification and the fourth response classification. In the example implementation, an individual with response classifications including high GSR, high pupil dilation, high negative FAC, and low positive FAC was determined to have a mental classification of frustrated.

In addition, the example instructions 600 are used to identify consecutive similar mental classifications (block 620). For example, the mental state determination module 202 of FIG. 2 assess the mental classifications and identifies consecutive mental classifications that are similar (e.g., two time periods during which the mental classification is similar). The example instructions 600 use the consecutive similar mental classification to determine the mental state (e.g., frustration, confusion, boredom, etc.) of the individual (block 622) using, for example the mental state determination module 202 of FIG. 2. In some examples, a mental state of a user is determined based on a degree of similarity between the first mental classification and the second mental classification. In the Adagio tea example implementation, an individual having a mental classification of frustrated for at least three consecutive time periods (for example) is assigned a mental state of frustrated.

Based on the determined mental state, the instructions are further executed to determine whether the mental state should be adjusted (block 624) to, for example, increase the positivity, decrease negativity, increase intensity, heighten a concentration and/or otherwise make a change to the mental state. For example, any individual operating the Adagio tea configurator who is experiencing frustration would be identified as a candidate in need of a mental state adjustment.

If it is determined that the mental state is to be adjusted, the instructions 600 include modifying the content (block 626). For example, the content modifier 222 of FIG. 2 may be used to adjust the content presented to the individual 104. For example, if the mental state indicates the individual is frustrated, the content modifier may display additional content, such as a helpful video, a coupon, quieter or louder audio, brighter or dimmer display brightness, more or less display items, etc. In some examples, the content modifies the first content to include second content and/or replaces the first content with second content based on the mental state. For example, the new or modified content presented to the individual 104 during the tea configuration process may also include, for example, a reduced choice of tea flavors to choose from to help the individual 104 decide, a suggested flavor of tea, a free gift (e.g., a tea infuser), a tutorial video, a suggested popular blend, etc. Additionally, in the example implementation, the individuals are presented with the option to swap the created tea blend for the tea blend of the month (e.g., a forced choice) and to add on items, such as cookies and a personalized mug (e.g., upsell) at the checkout.

After content has been modified (block 626), the control returns to block 602 and the modified content is presented to the individual and the example instructions 600 continue with the data gathering and analysis disclosed above. However, if it is determined that the mental state does not need to be adjusted (block 624), the example instructions are also used to determine whether or not to continue monitoring the individual (block 628). For example, if the mental state determination module 202 decides to continue monitoring the individual 104, control returns to block 604 and monitoring continues. However, if it is determined that monitoring is not to continue (block 628), monitoring ceases and the process 600 is complete (block 630). In the example implementation, the system continued to monitor the individual through the entire experience with the tea configurator and the process was designated as complete after the individual completed the checkout process. The results of the particular example implementation showed a positive impact on the amount of money spent by individuals receiving new or modified content based on the determined mental state (i.e., the individuals in the minimal and maximal adaptation groups spent more than the individuals in the random and control groups), with the maximal adaptation spending a slightly higher amount.

FIG. 7 is a flowchart representative of example machine-readable instructions or process 700 that may be executed for adjusting a baseline and/or threshold (using, for example, the example systems of FIGS. 1 and/or 2). The example instructions 700 include presenting content to one of more individuals that does not include a stimulus or target material (e.g., neutral or background media) (block 702). For example, the example presentation device 102 of FIG. 1 may be used to present content to an individual including, for example, a website containing a news article, an entertainment video, ambient audio etc.

The example instructions 700 include monitoring biometric responses (block 704). For example, one or more of the example sensors (e.g., the camera 114, the biometric sensing clothing 116, the biometric sensing bracelet 118, and/or the first, second, and Nth modality sensors 204, 206, 208) measures the response of the individual 104 to the content, which may include a biometric response, a neurophysiological response, and/or a behavioral response.

A baseline response is determined (block 706), using for example the baseline generator 218 if FIG. 2. The baseline may be used to identify biometric responses of the individual when in an inactive, unengaged, or unstimulated state (e.g., a passive state). The example instructions 700 also include establishing a threshold (block 708). The threshold may be determined by one of the components of the example system 200 of FIG. 2 (e.g., the response classifier 214 and/or baseline generator 218) in some examples, and in other examples, the threshold may be imported into the example system 200. The threshold values used in the example process 700 are set to indicate when a biometric response has deviated from the individual's baseline by an amount sufficient to signify that a change in a response has occurred.

The example instructions 700 also include presenting the individual with content that includes stimulus and/or target material (block 710). For example, the presentation device 102 of FIG. 1 maybe used to present a website (such as, for example, the tea configurator detailed above) to an individual. Further biometric responses are monitored (block 712) and compared to the current baseline and/or threshold (block 714).

The example instructions 700 are executed to determine if a period of time elapses in which the threshold has not been triggered (block 716). Triggering the threshold may mean, for example, meeting a threshold, crossing or exceeding a threshold, falling without or outside of a threshold range, etc. For example, the example system 200 analyzes the monitored biometric responses over time and continually compares the responses to the threshold, which was established in relation to the individual's baseline. In some examples, the individual's heart rate may be monitored to determine if the heart rate moves higher than 10 bmp over a baseline heart rate, or if the heart exceeds an absolute value change, or if the heart rate passes 80 bmp, and/or any other suitable or desired metrics. If the threshold has been triggered within the established time period, the individual's responses are continued to be monitored (block 712).

However, the threshold has not been triggered within the set time period (block 716), the example instructions 700 are executed to determine if the content has been modified (block 718) and, if not, content is modified (block 720), presented to the individual (block 710), and monitoring continues (block 712). The content may be modified, for example, in accordance with the example systems 100, 200 of FIGS. 1 and 2 and/or the process 600 of FIG. 6.

If the content has been modified (block 718), the example instructions 700 adjust the individual's baseline and/or reestablishes the threshold relative to the baseline (block 722) using, for example, the example system 200 including the baseline generator 218 as disclosed above. For example, if the individual is experiencing frustration and adjustments are made the content to change the individual's biometric responses (and, thus, mental state), but the system continues to read the individual's response as frustrated, there may be an indication that the adjusted content is not sufficient to change the individual's response to a more positive response.

Additionally or alternatively, this may be an indication that the threshold set, with respect to the baseline, is insufficient to detect a change in response. For example, if an individual has a baseline heart rate of 75 bpm and a threshold is set to a 5 bpm change (plus or minus), the change may determine when a person is experiencing boredom or frustration. If the person has a change of 10 bpm, the threshold has been crossed. There may be a desire to present modified content to the individual to change the response back to a positive response as indicated by the heart rate crossing the threshold back toward the 75 bpm baseline. New content may be provided, which alters the individual's 10 bmp change to 8 bmp but does not cross the 5 bmp threshold. This change indicates that the altered content is effective in changing the responses to the desired response. However, the change is not enough to trigger threshold and, therefore, goes undetected. This may cause the content provider to abandon the content modification, may ultimately be effective for changing the response to the desired response, or cause the content provider to overcompensate resulting in further and unnecessary modification of the content. With the present example systems and processes, the threshold may be adjusted to, for example a change of 2 bmp, for a more fine detection of responses changes. This advancement provides the content with enhanced detection capabilities and advanced knowledge of the effectiveness in content modification in causes an individual to have a desired response.

In addition, there are examples in which the baseline itself is to be changed. For example, if a content provider would like to know when an individual has a change in heart rate when the measurements already exceed the threshold and/or continuously exceed the threshold for a period of time, the baseline is adjusted to reflect the changes in heart rate at levels higher than the previous baseline. In some examples, the baseline may be changed based on task. A low stress task (e.g., buying a toothbrush) may have a lower baseline for heart rate than a high stress task (e.g., configuring a car) because the individual is more likely have a higher heart rate while performing the higher stress task and would likely continuously exceed a baseline for a lower stress task unless the baseline is adjusted according to the task. In some examples, the length of time for which the task is performed affects the change in the baseline.

Figure 8:
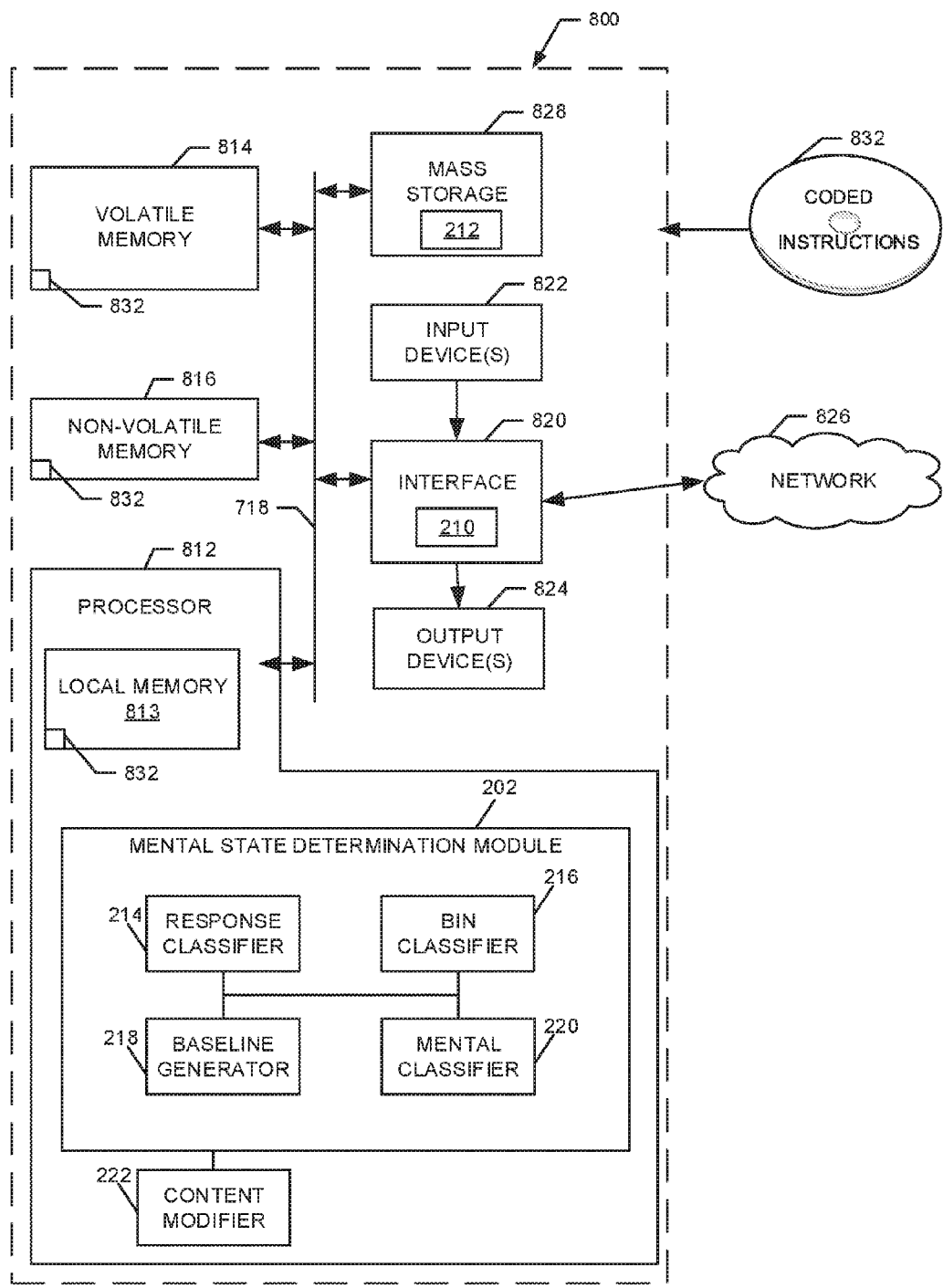
FIG. 8 is a block diagram of an example processor platform structured to execute the example machine-readable instructions of FIGS. 6 and 7 implemented by the example systems of FIGS. 1 and/or 2.

FIG. 8 is a block diagram of an example processor platform 800 capable of executing the instructions of FIGS. 6 and 7 to implement the apparatus and systems of FIGS. 1 and 2 including for example, the mental state determination module 202, the response classifier 214, the bin classifier 216, the baseline generator 218 and the mental classifier 220 and/or content modifier 222 of FIG. 2. The processor platform 800 can be, for example, a server, a personal computer, a mobile device (e.g., a cell phone, a smart phone), a personal digital assistant (PDA), an Internet appliance, a DVD player, a CD player, a digital video recorder, a Blu-ray player, a gaming console, a personal video recorder, a set top box, or any other type of computing device.

The processor platform 800 of the illustrated example includes a processor 812. The processor 812 of the illustrated example is hardware. For example, the processor 812 can be implemented by one or more integrated circuits, logic circuits, microprocessors or controllers from any desired family or manufacturer.

The processor 812 of the illustrated example includes a local memory 813 (e.g., a cache). The processor 812 of the illustrated example is in communication with a main memory including a volatile memory 814 and a non-volatile memory 816 via a bus 818. The volatile memory 814 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 816 may be implemented by flash memory and/or any other desired type of memory device. Access to the main memory 814, 816 is controlled by a memory controller.

The processor platform 800 of the illustrated example also includes an interface circuit 820. The interface circuit 820 may be implemented by any type of interface standard, such as an Ethernet interface, a universal serial bus (USB), and/or a PCI express interface.

In the illustrated example, one or more input devices 822 are connected to the interface circuit 820. The input device(s) 822 permit(s) a user to enter data and commands into the processor 812. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 824 are also connected to the interface circuit 820 of the illustrated example. The output devices 824 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). The interface circuit 820 of the illustrated example, thus, typically includes a graphics driver card, a graphics driver chip or a graphics driver processor.

The interface circuit 820 of the illustrated example also includes a communication device such as a transmitter, a receiver, a transceiver, a modem and/or network interface card to facilitate exchange of data with external machines (e.g., computing devices of any kind) via a network 826 (e.g., an Ethernet connection, a digital subscriber line (DSL), a telephone line, coaxial cable, a cellular telephone system, etc.).

The processor platform 800 of the illustrated example also includes one or more mass storage devices 828 for storing software and/or data. Examples of such mass storage devices 828 include floppy disk drives, hard drive disks, compact disk drives, Blu-ray disk drives, RAID systems, and digital versatile disk (DVD) drives.

The coded instructions 832 of FIG. 8 may be stored in the mass storage device 828, in the volatile memory 814, in the non-volatile memory 816, and/or on a removable tangible computer readable storage medium such as a CD or DVD.

From the foregoing, it will appreciate that the above disclosed methods, apparatus and articles of manufacture are operative to provide the individual with a better experience when interacting with media content, including websites, by altering content and/or presenting new content based on a mental state of the individual while viewing and/or interacting with the content.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A method to adjust content presented to an individual, the method comprising:

measuring, via a first modality sensor, a first response of the individual to first content during a first time frame;

determining a first response classification based on a first comparison of the first response and a first threshold;

measuring, via a second modality sensor, a second response of the individual to the first content during the first time frame;

determining a second response classification based on a second comparison of the second response to a second threshold;

determining a first mental classification of the individual based on combining the first response classification and the second response classification;

determining a first baseline during the first time frame, at least one of the first threshold or second threshold based on the first baseline;

measuring, via the first modality sensor, a third response of the individual to the first content during a second time frame;

measuring, via the second modality sensor, a fourth response of the individual to the first content during the second time frame;

adjusting the first baseline to a second baseline based on at least one of the third response or the fourth response in the second time frame;

adjusting at least one of the first threshold to a third threshold or second threshold to a fourth threshold based on the second baseline;

determining a third response classification based on a third comparison of the third response and the third threshold;

determining a fourth response classification based on a fourth comparison of the fourth response and the fourth threshold;

determining a second mental classification of the individual based on combining the third response classification and the fourth response classification;

determining a mental state of a user based on a degree of similarity between the first mental classification and the second mental classification; and at least one of modifying the first content to include second content or replacing the first content with second content based on the mental state.

2. The method of claim 1, the first modality sensor including a galvanic skin response sensor.

3. The method of claim 2, the second modality sensor including a pupil dilation sensor.

4. The method of claim 3, further including generating a cognitive load index based on data from the pupil dilation sensor, the cognitive load index representative of how much of a maximum information processing capacity of the individual is being used.

5. The method of claim 1, the second time frame partially overlapping the first time frame.

6. The method of claim 1 further including:
measuring, via a third modality sensor, a fifth response of the individual to the first content during the first time frame;
determining a fifth response classification based on a fifth comparison of the fifth response and a fifth threshold, the first mental classification of the individual based on combining the first response classification and the second response classification further with the fifth response classification;
measuring, via the third modality sensor, a sixth response of the individual to the first content during the second time frame; and
determining a sixth response classification based on a sixth comparison of the sixth response and the fifth threshold, the second mental classification of the individual based on combining the third response classification and the fourth response classification further with the sixth response classification.

7. The method of claim 6, the third modality sensor including a facial action coding sensor.

8. The method of claim 6, the third modality sensor including an eye tracking sensor.

9. The method of claim 1, the second content to increase a positivity level of the mental state.

10. The method of claim 9, the second content to at least one of induce a purchase or increase a total spend amount on a purchase.

11. A system comprising:
a first modality sensor;
a second modality sensor;
a processor to:
measure, via the first modality sensor, a first response of an individual to first content during a first time frame;
determine a first response classification based on a first comparison of the first response and a first threshold;
measure, via the second modality sensor, a second response of the individual to the first content during the first time frame;
determine a second response classification based on a second comparison of the second response to a second threshold;
determine a first baseline during the first time frame, at least one of the first threshold or second threshold based on the first baseline;
determine a first mental classification of the individual based on combining the first response classification and the second response classification;
measure, via the first modality sensor, a third response of the individual to the first content during a second time frame;
measure, via the second modality sensor, a fourth response of the individual to the first content during the second time frame;
adjust the first baseline to a second baseline based on at least one of the third response or the fourth response in the second time frame;
adjust at least one of the first threshold to a third threshold or the second threshold to a fourth threshold based on the second baseline;
determine a third response classification based on a third comparison of the third response and the third threshold;
determine a fourth response classification based on a fourth comparison of the fourth response to the fourth threshold;
determine a second mental classification of the individual based on combining the third response classification and the fourth response classification;
determine a mental state of a user based on a degree of similarity between the first mental classification and the second mental classification; and
at least one of modify the first content to include second content or replace the first content with second content based on the mental state.

12. The system of claim 11, the first modality sensor including a galvanic skin response sensor.

13. The system of claim 12, the second modality sensor including a pupil dilation sensor, and the processor is to generate a cognitive load index based on data from the pupil dilation sensor, the cognitive load index representative of how much of a maximum information processing capacity of the individual is being used.

14. The system of claim 11, the second time frame partially overlapping the first time frame.

15. The system of claim 11, the processor to further:
measure, via a third modality sensor, a fifth response of the individual to the first content during the first time frame;
determine a fifth response classification based on a fifth comparison of the fifth response and a fifth threshold, the first mental classification of the individual based on combining the first response classification and the second response classification further with the fifth response classification;
measure, via the third modality sensor, a sixth response of the individual to the first content during the second time frame; and
determine a sixth response classification based on a sixth comparison of the sixth response and the fifth threshold, the second mental classification of the individual based on combining the third response classification and the fourth response classification further with the sixth response classification.

16. The system of claim 15, the third modality sensor including at least one of a facial action coding sensor or an eye tracking sensor.

17. The system of claim 11, the second content to increase a positivity level of the mental state, the second content to at least one of induce a purchase or increase a total spend amount on a purchase.

18. A tangible computer readable storage medium comprising instructions that, when executed, causes a processor of a content presentation device to at least:
measure, via a first modality sensor, a first response of an individual to first content during a first time frame;
determine a first response classification based on a first comparison of the first response and a first threshold;
measure, via a second modality sensor, a second response of the individual to the first content during the first time frame;
determine a second response classification based on a second comparison of the second response to a second threshold;
determine a first baseline during the first time frame, at least one of the first threshold or second threshold based on the first baseline;

determine a first mental classification of the individual based on combining the first response classification and the second response classification;

measure, via the first modality sensor, a third response of the individual to the first content during a second time frame;

measure, via the second modality sensor, a fourth response of the individual to the first content during the second time frame;

adjust the first baseline to a second baseline based on the third response or the fourth response in the second time frame;

adjust at least one of the first threshold to a third threshold or the second threshold to a fourth threshold based on the second baselines;

determine a third response classification based on a third comparison of the third response and the third threshold;

determine a fourth response classification based on a fourth comparison of the fourth response to the fourth threshold;

determine a second mental classification of the individual based on combining the third response classification and the fourth response classification;

determine a mental state of a user based on a degree of similarity between the first mental classification and the second mental classification; and at least one of modify the first content to include second content or replace the first content with second content based on the mental state.

19. The medium of claim 18, wherein the instructions, when executed, further cause the processor to:

measure, via a third modality sensor, a fifth response of the individual to the first content during the first time frame;

determine a fifth response classification based on a fifth comparison of the fifth response and a fifth threshold, the first mental classification of the individual based on combining the first response classification and the second response classification further with the fifth response classification;

measure, via the third modality sensor, a sixth response of the individual to the first content during the second time frame; and determine a sixth response classification based on a sixth comparison of the sixth response and the fifth threshold, the second mental classification of the individual based on combining the third response classification and the fourth response classification further with the sixth response classification.

20. The medium of claim 18, wherein the instructions, when executed, further cause the processor to generate a cognitive load index based on data from a pupil dilation sensor, the cognitive load index representative of how much of a maximum information processing capacity of the individual is being used.

* * * * *